United States Patent
Gong et al.

(10) Patent No.: US 10,059,721 B2
(45) Date of Patent: Aug. 28, 2018

(54) SUBSTITUTED THIENO[3,2-B]PYRAZINES FOR INHIBITING CANCER CELL PROLIFERATION AND INDUCING CANCER CELL APOPTOSIS

(71) Applicant: DONGGUK UNIVERSITY INDUSTRY-ACADEMIC COOPERATION FOUNDATION, Seoul (KR)

(72) Inventors: Young Dae Gong, Seoul (KR); Se Hun Kwak, Seoul (KR); Eun Sil Lee, Seoul (KR)

(73) Assignee: DONGGUK UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/533,076

(22) PCT Filed: Dec. 3, 2015

(86) PCT No.: PCT/KR2015/013150
§ 371 (c)(1),
(2) Date: Jun. 5, 2017

(87) PCT Pub. No.: WO2016/093554
PCT Pub. Date: Jun. 16, 2016

(65) Prior Publication Data
US 2017/0320890 A1    Nov. 9, 2017

(30) Foreign Application Priority Data
Dec. 8, 2014 (KR) ........................ 10-2014-0175121

(51) Int. Cl.
*A61K 31/4985* (2006.01)
*C07D 487/04* (2006.01)
*C07D 495/04* (2006.01)

(52) U.S. Cl.
CPC .................. *C07D 495/04* (2013.01)

(58) Field of Classification Search
CPC .......................... A61K 31/4985; C07D 487/04
USPC .......................................... 514/249; 544/350
See application file for complete search history.

(56) References Cited

U.S. PATENT DOCUMENTS

| 6,683,184 B2 | 1/2004 | Cho et al. |
| 8,314,100 B2 | 11/2012 | Gong et al. |
| 8,669,256 B2 | 3/2014 | Folmer et al. |
| 2006/0183758 A1 | 8/2006 | Beard et al. |

FOREIGN PATENT DOCUMENTS

| KR | 1020140090500 A | | 12/2014 |
| WO | 2000052001 A1 | | 9/2000 |
| WO | 2006054830 A1 | | 5/2006 |
| WO | WO 16/093554 | * | 6/2016 |

OTHER PUBLICATIONS

Jordan, V. C. Nature Reviews: Drug Discovery, Feb. 2003, 205.*
Hackam, et al. JAMA, 296(14), 2006, 1731-1732.*
Kolli, Sunder Kumar et al., "NaSH in the construction of thiophene ring fused with N-heterocycles: A rapid and inexpensive synthesis of novel small molecules as potential inducers of apoptosis" Bioorganic & Medicinal Chemistry Letters 24 (2014) 4460-4465.
International Search Report, PCT/KR2015/013150 [KIPO] dated Sep. 9, 2016.
Notice of Allowance Korean Patent Application No. 10-2014-0175121 dated Mar. 22, 2017.

* cited by examiner

*Primary Examiner* — Douglas M Willis
(74) *Attorney, Agent, or Firm* — Edwin S. Flores; Daniel J. Chalker; Chalker Flores, LLP

(57) ABSTRACT

The present invention relates to a novel 4-(aryl)-N-(2-alkoxythieno[3,2-b]pyrazin-3-yl)-piperazin-1-carboxamide derivative compound useful in the prevention or treatment of cancer; a preparation method thereof; and a pharmaceutical composition comprising the same. The novel 4-(aryl)-N-(2-alkoxythieno[3,2-b]pyrazin-3-yl)-piperazin-1-carboxamide derivative compound of the present invention can effectively inhibit the growth of proliferating cells, and thus can be useful in the prevention or treatment of cancer.

15 Claims, No Drawings

SUBSTITUTED THIENO[3,2-B]PYRAZINES FOR INHIBITING CANCER CELL PROLIFERATION AND INDUCING CANCER CELL APOPTOSIS

CROSS-REFERENCE TO RELATED APPLICATIONS

This application is the National Stage of International Application No. PCT/KR2015/013150, filed on Dec. 3, 2015 claiming the priority of KR 10-2014-0175121, filed on Dec. 8, 2014, the content of each of which is incorporated by reference herein.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to a novel 4-(aryl)-N-(2-alkoxythieno[3,2-b]pyrazin-3-yl)-piperazin-1-carboxamide derivative compound useful in the prevention or treatment of cancer; a preparation method thereof; and a pharmaceutical composition comprising the same.

2. Description of the Related Art

Cancer is a serious disease which is the leading cause of death in Korea. Although numerous researches have been carried out in order to overcome cancer, it is considered as an incurable disease that is still required to be overcome. Cancer is a disease that occurs due to failing to regulate cell growth, thereby referring to a malignant tumor. Cancer cells uncontrollably divide and grow to form malignant tumors, which in turn invade adjacent tissues of the body. Additionally, cancer cells metastasize not only to adjacent tissues but also to distance tissues via lymphatic system or blood flow. Conventional treatments for cancer include surgery, chemotherapy, radiation therapy, etc. Among these treatments, chemotherapy using anticancer drugs is widely used for cancer treatment, and it is one of well-established treatment methods. These anticancer drugs intervene in the metabolic pathway of cancer cells to block the process of replication, transcription, and translation of DNA through the direct interaction with DNA; to interfere with the synthesis of nucleic acid precursors; and to inhibit cell division, thereby showing toxicity to cells. Accordingly, anticancer drugs cause fatal damage to normal cells, and as a result, the drugs have various side effects, i.e., a reduction in the number of blood cells, such as white blood cells, platelets, erythrocytes, etc., due to marrow destruction; hair loss due to destruction of hair follicle cells; menstrual irregularity and male sterility due to side effects on ovaries and testicles; stomatitis due to destruction of mucosal cells in digestive organs; nausea-vomiting, swallowing difficulty, and maldigestion; diarrhea; nephrotoxicity due to tubulorrhexis; peripheral neuritis and general weakness due to a neurological disorder; vascular disorders such as pain in blood vessels and rash; discoloration of skins and nails; etc. Therefore, it is still required to develop an anticancer drug that can overcome side effects of anticancer drugs currently used in the clinic, reduce toxicity to normal cells, and can show effects on selective apoptosis of cancer cells.

In connection with such efforts, the present inventors have conducted prior invention searches, and noticed that a 1-[(2-methoxyquinoxalin-3-yl)aminocarbonyl]-4-arylpiperazine derivative has low toxicity while showing an excellent anticancer activity (U.S. Pat. No. 6,683,184). In addition, it was confirmed that since the 1-[(2-methoxyquinoxalin-3-yl)aminocarbonyl]-4-arylpiperazine derivative is a compound in which positions 5, 6, 7, and 8 of a quinoxaline ring are all substituted with hydrogen, there was a limit to the drug efficacy and the anticancer activity of cancer cells. Therefore, in order to overcome such limitation, the present inventors have developed a novel anticancer drug in which a substituent other than hydrogen is introduced at position 5 of the quinoxaline ring (U.S. Pat. No. 8,314,100).

BRIEF SUMMARY OF THE INVENTION

The present inventors have made their intensive research efforts to find a novel compound having an anticancer activity, containing thieno[3,2-b]pyrazine in addition to the quinoxaline in a mother nucleus. As a result, the present inventors have discovered a series of novel 4-(aryl)-N-(2-alkoxythieno[3,2-b]pyrazin-3-yl)-piperazin-1-carboxamide derivative compounds, and confirmed that these compounds have an excellent effect of suppressing the growth and proliferation of cancer cells, thereby completing the present invention.

An object of the present invention is to provide a novel 4-(aryl)-N-(2-alkoxythieno[3,2-b]pyrazin-3-yl)-piperazin-1-carboxamide derivative compound or a pharmaceutically acceptable salt thereof.

Another object of the present invention is to provide a method for preparing the compound.

A further object of the present invention is to provide a pharmaceutical composition for preventing or treating cancer, comprising the compound or the pharmaceutically acceptable salt thereof as an active ingredient.

A still further object of the present invention is to provide a method for preventing or treating a cancer disease from a subject, comprising a step of administering the pharmaceutical composition to a subject in need thereof.

The novel 4-(aryl)-N-(2-alkoxythieno[3,2-b]pyrazin-3-yl)-piperazin-1-carboxamide derivative compounds of the present invention can effectively suppress the growth of proliferating cells, and thus can be useful for the prevention or treatment of cancer.

BRIEF DESCRIPTION OF THE SEVERAL VIEWS OF THE DRAWINGS

Not Applicable

DETAILED DESCRIPTION OF THE INVENTION

In order to overcome the above-mentioned problem, the present invention provides a compound represented by the following Formula 1 or a pharmaceutically acceptable salt thereof:

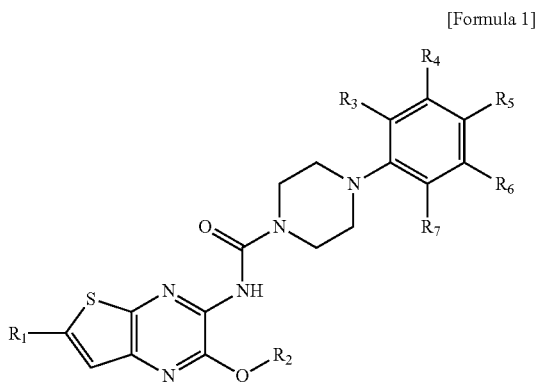

[Formula 1]

wherein, in the above formula, $R_1$ is hydrogen or halogen; $R_2$ is linear or branched $C_{1-6}$ alkyl; and $R_3$ to $R_7$ are each independently hydrogen, halogen, linear, or branched $C_{1-6}$ alkyl, linear or branched $C_{1-6}$ haloalkyl, $C_{1-6}$ alkoxy, or $C_{1-6}$ haloalkoxy.

Preferably, in the above formula, $R_1$ may be hydrogen or chloro.

Preferably, in the above formula, $R_2$ may be methyl, ethyl, or isopropyl.

Preferably, in the above formula, $R_3$ to $R_7$ may each independently be hydrogen, fluoro, methyl, trifluoromethyl, methoxy, or trifluoromethoxy.

More preferably, in the above formula, $R_3$, $R_5$, and $R_7$ may be all hydrogen; and $R_4$ and $R_6$ may be the same or different, and may each independently be fluoro, methyl, trifluoromethyl, methoxy, or trifluoromethoxy.

Preferably, the compound represented by Formula 1 may be

1) N-(6-chloro-2-methoxythieno[3,2-b]pyrazin-3-yl)-4-(3,5-dimethoxyphenyl)piperazin-1-carboxamide,
2) N-(6-chloro-2-methoxythieno[3,2-b]pyrazin-3-yl)-4-(3,5-dimethylphenyl)piperazin-1-carboxamide,
3) N-(6-chloro-2-methoxythieno[3,2-b]pyrazin-3-yl)-4-(3,5-difluorophenyl)piperazin-1-carboxamide,
4) N-(6-chloro-2-ethoxythieno[3,2-b]pyrazin-3-yl)-4-(3,5-dimethoxyphenyl)piperazin-1-carboxamide,
5) N-(6-chloro-2-ethoxythieno[3,2-b]pyrazin-3-yl)-4-(3,5-dimethylphenyl)piperazin-1-carboxamide
6) N-(6-chloro-2-ethoxythieno[3,2-b]pyrazin-3-yl)-4-(3,5-difluorophenyl)piperazin-1-carboxamide,
7) N-(6-chloro-2-isopropoxythieno[3,2-b]pyrazin-3-yl)-4-(3,5-dimethoxyphenyl)piperazin-1-carboxamide,
8) N-(6-chloro-2-isopropoxythieno[3,2-b]pyrazin-3-yl)-4-(3,5-dimethylphenyl)piperazin-1-carboxamide,
9) N-(6-chloro-2-isopropoxythieno[3,2-b]pyrazin-3-yl)-4-(3,5-difluorophenyl)piperazin-1-carboxamide,
10) 4-(3,5-dimethoxyphenyl)-N-(2-methoxythieno[3,2-b]pyrazin-3-yl)piperazin-1-carboxamide,
11) 4-(3,5-dimethylphenyl)-N-(2-methoxythieno[3,2-b]pyrazin-3-yl)piperazin-1-carboxamide,
12) 4-(3,5-difluorophenyl)-N-(2-methoxythieno[3,2-b]pyrazin-3-yl)piperazin-1-carboxamide,
13) 4-(3,5-dimethoxyphenyl)-N-(2-ethoxythieno[3,2-b]pyrazin-3-yl)piperazin-1-carboxamide,
14) 4-(3,5-dimethylphenyl)-N-(2-ethoxythieno[3,2-b]pyrazin-3-yl)piperazin-1-carboxamide,
15) 4-(3,5-difluorophenyl)-N-(2-ethoxythieno[3,2-b]pyrazin-3-yl)piperazin-1-carboxamide,
16) 4-(3,5-dimethoxyphenyl)-N-(2-isopropoxythieno[3,2-b]pyrazin-3-yl)piperazin-1-carboxamide,
17) 4-(3,5-dimethylphenyl)-N-(2-isopropoxythieno[3,2-b]pyrazin-3-yl)piperazin-1-carboxamide,
18) 4-(3,5-difluorophenyl)-N-(2-isopropoxythieno[3,2-b]pyrazin-3-yl)piperazin-1-carboxamide,
19) N-(2-methoxythieno[3,2-b]pyrazin-3-yl)-4-(3-methyl-5-(trifluoromethoxy)phenyl)piperazin-1-carboxamide,
20) N-(2-methoxythieno[3,2-b]pyrazin-3-yl)-4-(3-(trifluoromethoxy)-5-(trifluoromethyl)phenyl)piperazin-1-carboxamide,
21) 4-(3-methoxy-5-methylphenyl)-N-(2-methoxythieno[3,2-b]pyrazin-3-yl)piperazin-1-carboxamide,
22) 4-(3-fluoro-5-methoxyphenyl)-N-(2-methoxythieno[3,2-b]pyrazin-3-yl)piperazin-1-carboxamide,
23) 4-(3-fluoro-5-methylphenyl)-N-(2-methoxythieno[3,2-b]pyrazin-3-yl)piperazin-1-carboxamide,
24) N-(2-methoxythieno[3,2-b]pyrazin-3-yl)-4-(3-(trifluoromethoxy)phenyl)piperazin-1-carboxamide,
25) 4-(3-methoxy-5-(trifluoromethoxy)phenyl)-N-(2-methoxythieno[3,2-b]pyrazin-3-yl)piperazin-1-carboxamide,
26) 4-(3-fluoro-5-(trifluoromethoxy)phenyl)-N-(2-methoxythieno[3,2-b]pyrazin-3-yl)piperazin-1-carboxamide, or
27) 4-(3-fluoro-5-(trifluoromethyl)phenyl)-N-(2-methoxythieno[3,2-b]pyrazin-3-yl)piperazin-1-carboxamide.

In the specific exemplary embodiments of the present invention, 27 types of the compounds were synthesized, and the constitution of these constituents is summarized in Table 1.

The compound of the present invention can exist in the form of a salt, especially a pharmaceutically acceptable salt. For the salt, a salt commonly used in the art, such as an acid-addition salt formed by a pharmaceutically acceptable free acid, can be used without limitation. As used herein, the term "pharmaceutically acceptable salt" refers to any organic or inorganic compound addition salt whose concentration has effective action because it is relatively non-toxic and harmless to the patients and whose side effects do not degrade the beneficial efficacy of the compound which is represented by Formula 1.

An acid-addition salt can be prepared by a conventional method. For example, after dissolving the compound in the excess amount of an acid solution, the salt is precipitated by the water-miscible organic solvent such as methanol, ethanol, acetone, or acetonitrile to prepare an acid-addition salt. In addition, the mixture of an equivalent amount of the compound and diluted acid with water or alcohol (i.e., glycol monomethylether) can be heated and subsequently dried by evaporation or filtrated under reduced pressure to obtain dried salt form thereof.

For the free acid, organic and inorganic acid may be used. For example, inorganic acid such as hydrochloric acid, phosphoric acid, sulfuric acid, nitric acid, tartaric acid, etc., and organic acid such as methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid, etc. may be used herein, but are not limited thereto.

Additionally, the pharmaceutically acceptable metal salt may be prepared using base. The alkali metal or alkaline earth metal salt can be obtained, for example, by after dissolving the compound in an excess amount of an alkali metal hydroxide or alkaline earth metal hydroxide solution, the insoluble salts in the compound are filtered and remaining filtrate is subject to evaporation and drying. Herein, it is pharmaceutically suitable to prepare sodium, potassium, or a calcium salt as the metal salt, but is not limited thereto. In addition, the corresponding silver salt can be obtained by reacting an alkali metal or alkaline earth metal salt with a suitable silver salt (e.g., silver nitrate).

The pharmaceutically acceptable salt of the compound of the present invention comprises a salt of an acidic or base group that may be present in the compound of Formula 1, unless otherwise indicated. For example, the pharmaceutically acceptable salt includes sodium, calcium, and potassium salts of hydroxy group, and other pharmaceutically acceptable salts of amino group, including hydrobromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate), etc. The salt may be prepared using a salt preparation method known in the art.

For the pharmaceutically acceptable salt of the compound represented by Formula 1 of the present invention, any salts may be used without limitation as long as they are salts of compounds which inhibit proliferation of cancer cells and show an effecting of inducing apoptosis, equivalently to the compound represented by Formula 1.

Additionally, the compound represented by Formula 1 according to the present invention includes not only a pharmaceutically acceptable salt but also a solvate such as a hydrate that can possibly be prepared therefrom, without limitation. The solvate of the compound represented by Formula 1 can be prepared from the compound represented by Formula 1 using a method known in the art.

Additionally, the compound represented by Formula 1 according to the present invention can be prepared in a crystalline or non-crystalline form. Further, when the compound of Formula 1 is prepared in a crystalline form, it may be randomly hydrated or solvated. In the present invention, the compound represented by Formula 1 may not only include a stoichiometric hydrate, but also include a compound containing various amounts of water. The solvate of the compound represented by Formula 1 according to the present invention includes both stoichiometric solvates and non-stoichiometric solvates.

In another aspect, the present invention provides a method for preparing a compound represented by the following Formula 1, comprising: a first step of preparing a compound represented by the following Formula 3 from a compound represented by the following Formula 2; and a second step of preparing the compound represented by the following Formula 1 by reacting the compound represented by the following Formula 3 with a compound represented by the following Formula 4:

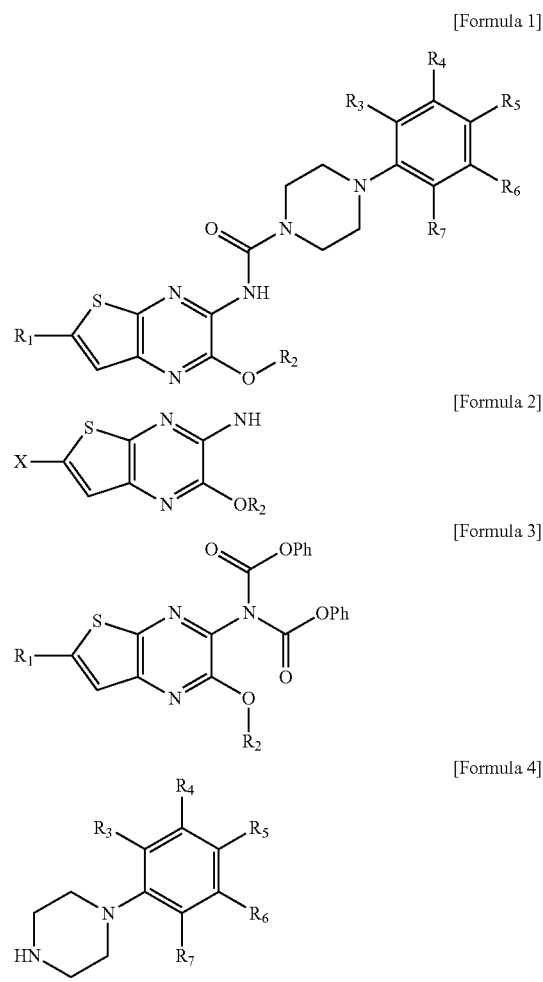

wherein, in the above formulas,
X is halogen; and
$R_1$ to $R_7$ are as defined above.
Preferably, X may be chloro.
Preferably, the method may further comprise a step of removing a halogen substituent before the first step, when the method is for preparing a compound wherein $R_1$ in the above formulas is hydrogen.
Preferably, the compound represented by Formula 2 may be synthesized from a 6-halopyrazine-2-amine compound.
More preferably, the compound represented by Formula 2 may be synthesized by:

i) a step of brominating a compound represented by the following Formula 5 to obtain a compound represented by the following Formula 6;

ii) a step of substituting the bromo in the compound represented by Formula 6 with trimethylsilylethynyl to obtain a compound represented by the following Formula 7;

iii) a step of carrying out a cyclization reaction of the compound represented by Formula 7 to form a compound represented by the following Formula 8;

iv) a step of halogenating the compound represented by Formula 8 to obtain a compound represented by the following Formula 9; and v) a step of selectively substituting the halogen on the pyrazine ring of the compound represented by Formula 9 with a $C_{1-6}$ alkoxy group, but is not limited thereto. In addition, as long as the compound represented by Formula 2 can be provided as a product, a synthesis method known in the art or the method partially modified therefrom may be carried out.

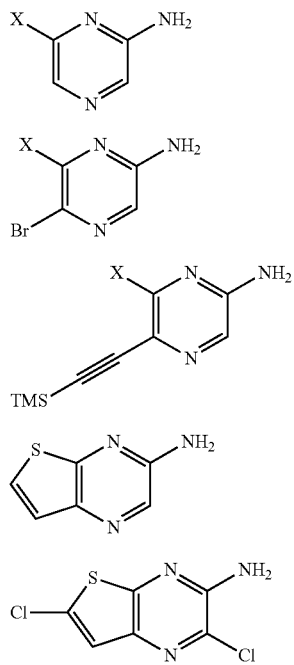

wherein, in the above formulas, X is halogen.

In the specific exemplary embodiments of the present invention, a 2-($C_{1-6}$ alkoxy)thieno[3,2-b]pyrazin-3-amine derivative was synthesized from a 6-halopyrazine-2-amine compound. Thereafter, a 4-(unsubstituted or substituted phenyl)-N-(2-($C_{1-6}$ alkoxy)thieno[3,2-b]pyrazin-3-yl)-piperazin-1-carboxamide derivative, which is the title compound, was synthesized therefrom.

In another aspect, the present invention provides a pharmaceutical composition for preventing or treating cancer, comprising the compound represented by Formula 1 or the pharmaceutically acceptable salt thereof as an active ingredient.

As used herein, the term "prevention" refers to all actions of suppressing or delaying the occurrence, spreading, and recurrence of cancer diseases by administration of the composition of the present invention. In addition, as used herein, the term "treatment" refers to all actions in which symptoms of the diseases are improved or advantageously altered by administration of the composition of the present invention.

The pharmaceutical composition of the present invention can prevent or treat cancer by suppressing proliferation of cancers cells and inducing apoptosis. Preferably, non-limiting examples of cancers that can be prevented or treated using the pharmaceutical composition of the present invention is colon cancer, breast cancer, pancreatic cancer, head and neck cancer, kidney cancer, lung cancer, colorectal adenocarcinoma, or other adenocarcinoma.

Preferably, the pharmaceutical composition according to the present invention may contain the compound represented by Formula 1 or the pharmaceutically acceptable salt thereof by 0.1 wt % to 75 wt %, more preferably 1 wt % to 50 wt %, based on the total weight of the composition.

The composition of the present invention can be used in the various forms such as oral dosage forms of powders, granules, tablets, capsules, suspensions, emulsions, syrups, aerosols and injections of a sterile injectable solution formulated by the conventional method to serve the purpose of each in accordance, can be administered through various routes including oral administration or intravenous, intraperitoneal, subcutaneous, rectal, and topical administration. The examples of suitable carrier, diluting agent, or diluent for example which can be included in this composition may be lactose, dextrose, sucrose, sorbitol, mannitol, xylitol, erythritol, maltitol, starch, acacia rubber, alginate, gelatin, calcium phosphate, calcium silicate, cellulose, methyl cellulose, amorphous cellulose, polyvinyl pyrrolidone, water, methyl hydroxy benzoate, propyl hydroxy benzoate, talc, magnesium stearate, and mineral oil. The composition of the present invention may further comprise fillers, anti-coagulants, lubricants, humectants, fragrances, emulsifiers, preservatives, etc.

Solid formulation agents for oral administration include tablets, pills, powders, granules, and capsules, and such solid dosage forms are formulated by mixing the composition in the present invention with one or more diluting agents, such as starch, calcium carbonate, sucrose, lactose, gelatin, etc. In addition, lubricants such as magnesium stearate and talc can be used in addition to simple diluting agents.

Liquid formulation agents for oral administration can be illustrated as suspensions, solutions, emulsions, syrups, etc., and can include various diluting agents such as humectants, sweeteners, fragrances, preservatives, etc., in addition to water, liquid paraffin which are commonly used as diluents.

Formulation agents for parenteral administration include sterile aqueous solutions, nonaqueous solvent, suspending agent, emulsion, lyophilization agent, and suppository agent. Nonaqueous solvent and suspending agent may include propylene glycol, polyethylene glycol, vegetable oil such as olive oil, and injectable esters such as ethyl oleate, etc. As substrates for the suppository formulation, Witepsol, Macrogol, twin 61, cacao butter, laurin butter, or glycerogelatin may be used. On the other hand, injections may include conventional additives such as solvents, isotonic agent, suspending agents, emulsifiers, stabilizers, preservatives, etc.

The composition of the present invention is administered in a pharmaceutically effective amount. As used herein, the term "pharmaceutically effective amount" refers to an amount sufficient to treat diseases at a reasonable benefit/risk ratio applicable to any medical treatment, and refers to an amount that does not cause side effects. In addition, the effective dosage level of the composition may be determined depending on factors, including the health condition of patients, the types of the disease, the severity of the disease, the activity of the drug, the patient's sensitivity to the drug, the administration method, the administration time, the route of administration, excretion rate, the duration of treatment, drugs concurrently used in combination with the composition, and other factors well known in the medical field. The composition of the present invention may be administered individually or in combination with other therapeutic agents, and may be administered sequentially or simultaneously with conventional therapeutic agents. The composition may be administered in a single or multiple dosage form. It is important to administer the composition in the minimum amount that can exhibit the maximum effect without causing side effects, in view of all the above-described factors, and it can be easily determined by one of ordinary skill in the art.

Specifically, the effective amount of the compound in the composition of the present invention can vary depending on the patient's age, sex, and body weight, and 1 mg to 100 mg in general, or 5 mg to 60 mg preferably per 1 kg of the body weight can be administered every day, every other day, or 1 to 3 times a day. However, the amount may be decreased or increased depending on the route of administration, the severity of the disease, sex, body weight, age, etc., and thus does not in any way limit the scope of the present invention.

The present invention also provides a method for preventing or treating a cancer disease from a subject, comprising a step of administering the pharmaceutical composition to a subject in need thereof.

As used herein, the term "subject" refers to an animal including a human who has the cancer or is likely to have the cancer, a monkey, a cow, a horse, a sheep, a pig, a chicken, a turkey, a quail, a cat, a dog, a mouse, a rat, a rabbit, or a guinea pig, and the disease can be effectively prevented or treated by administering the pharmaceutical composition of the present invention to a subject. The pharmaceutical composition of the present invention can be administered concurrently with conventional therapeutic agents.

As used herein, the term "administration" refers to introduction of a predetermined material to a patient by any appropriate methods, and the administration route of the composition of the present invention can be administered to any general route as long as the composition reaches the target tissues. The pharmaceutical composition of the present invention may be administered through intraperitoneal administration, intravenous administration, intramuscular administration, subcutaneous administration, intradermal administration, oral administration, topical administration, intranasal administration, intrapulmonary administration, or intrarectal administration, but is not limited thereto. Additionally, the pharmaceutical composition of the present invention may also be administered by any device capable of transferring the active agent to the target cells. Preferable administration mode and formulation are an intravenous injection, a subcutaneous injection, an intradermal injection, an intramuscular injection, instillation, etc. Injectable formulations can be prepared using aqueous solvents, such as physiological saline, Ringer's solution, etc., or non-aqueous solvents, such as vegetable oils, higher fatty acid esters (e.g., ethyl oleate), alcohols (e.g., ethanol, benzyl alcohol, propylene glycol, glycerin, etc.). In addition, the composition may comprise pharmaceutically acceptable carriers, including a stabilizer for preventing degeneration (e.g., ascorbic acid, sodium bisulfate, sodium pyrosulfite, BHA, tocopherol, EDTA, etc.), an emulsifier, a buffering agent for pH control, and a preservative for inhibiting microbial growth (e.g., phenylmercuric nitrate, thimerosal, benzalkonium chloride, phenol, cresol, benzylalcohol, etc.).

The term "therapeutically effective amount" used in combination with the active ingredient in the present invention refers to an amount of the compound represented by Formula 1, which is effective for preventing or treating the target disease, or the pharmaceutically acceptable salt thereof.

In addition to the compound represented by Formula 1 or the pharmaceutically acceptable salt thereof used as an active ingredient, the pharmaceutical composition of the present invention may further comprise known drugs used for the prevention or treatment of each known disease depending on the types of diseases to be prevented or treated. For example, when used for the prevention or treatment of cancer diseases, the composition may further comprise anticancer agents known in the art, in addition to a (tetrahydroquinoline-4-yl)malonate derivative compound or a pharmaceutically acceptable salt thereof used as an active ingredient. Further, the composition can be used in combination with other therapy known for treating these diseases. Other therapy includes chemotherapy, radiation therapy, hormonal therapy, bone marrow transplantation, stem-cell replacement therapy, other biological therapy, and immunotherapy, but is not limited thereto.

Examples of the anti-cancer agent which can be included in the pharmaceutical composition in the present invention include mechloethamine, chlorambucil, phenylalanine, mustard, cyclophosphamide, ifosfamide, carmustine (BCNU), lomustine (CCNU), streptozotocin, busulfan, thiotepa, cisplatin, and carboplatin as DNA alkylating agents; dactinomycin (actinomycin D), doxorubicin (adriamycin), daunorubicin, idarubicin, mitoxantrone, plicamycin, mitomycin, and C bleomycin as anti-cancer antibiotics; and vincristine, vinblastine, paclitaxel, docetaxel, etoposide, teniposide, topotecan, and iridotecan as plant alkaloids, but are not limited thereto.

Hereinbelow, the present invention will be described in detail with accompanying exemplary embodiments. However, the exemplary embodiments disclosed herein are only for illustrative purposes and should not be construed as limiting the scope of the present invention.

The constitution of 27 substituents of the compound represented by Formula 1, synthesized in the specific exemplary embodiments of the present invention, is summarized in Table 1 below together with LC/MS data.

[Formula 1]

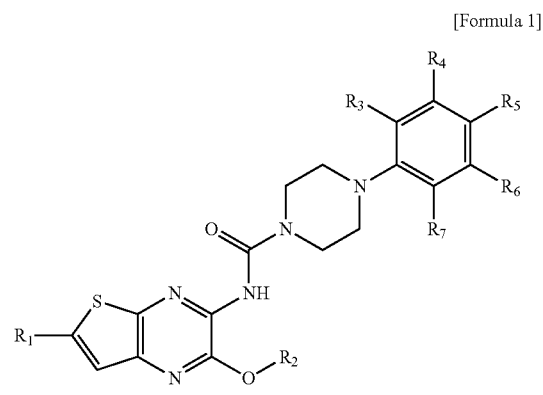

TABLE 1

| Example # | R1 | R2 | R3 | R4 | R5 | R6 | R7 | LC/MS (ESI) |
|---|---|---|---|---|---|---|---|---|
| 1 | Cl | methyl | H | methoxy | H | methoxy | H | 465 [M + H]+ |
| 2 | Cl | methyl | H | methyl | H | methyl | H | 433 [M + H]+ |
| 3 | Cl | methyl | H | fluoro | H | fluoro | H | 441 [M + H]+ |
| 4 | Cl | ethyl | H | methoxy | H | methoxy | H | 479 [M + H]+ |
| 5 | Cl | ethyl | H | methyl | H | methyl | H | 447 [M + H]+ |
| 6 | Cl | ethyl | H | fluoro | H | fluoro | H | 455 [M + H]+ |
| 7 | Cl | isopropyl | H | methoxy | H | methoxy | H | 492 [M + H]+ |
| 8 | Cl | isopropyl | H | methyl | H | methyl | H | 460 [M + H]+ |
| 9 | Cl | isopropyl | H | fluoro | H | fluoro | H | 468 [M + H]+ |
| 10 | H | methyl | H | methoxy | H | methoxy | H | 430 [M + H]+ |
| 11 | H | methyl | H | methyl | H | methyl | H | 398 [M + H]+ |
| 12 | H | methyl | H | fluoro | H | fluoro | H | 406 [M + H]+ |
| 13 | H | ethyl | H | methoxy | H | methoxy | H | 445 [M + H]+ |
| 14 | H | ethyl | H | methyl | H | methyl | H | 413 [M + H]+ |
| 15 | H | ethyl | H | fluoro | H | fluoro | H | 420 [M + H]+ |
| 16 | H | isopropyl | H | methoxy | H | methoxy | H | 458 [M + H]+ |
| 17 | H | isopropyl | H | methyl | H | methyl | H | 426 [M + H]+ |
| 18 | H | isopropyl | H | fluoro | H | fluoro | H | 434 [M + H]+ |
| 19 | H | methyl | H | trifluoromethoxy | H | methyl | H | 468 [M + H]+ |
| 20 | H | methyl | H | trifluoromethoxy | H | trifluoromethyl | H | 522 [M + H]+ |
| 21 | H | methyl | H | methoxy | H | methyl | H | 414 [M + H]+ |
| 22 | H | methyl | H | methoxy | H | fluoro | H | 418 [M + H]+ |
| 23 | H | methyl | H | methyl | H | fluoro | H | 402 [M + H]+ |
| 24 | H | methyl | H | trifluoromethoxy | H | H | H | 454 [M + H]+ |
| 25 | H | methyl | H | trifluoromethoxy | H | methoxy | H | 484 [M + H]+ |
| 26 | H | methyl | H | trifluoromethoxy | H | fluoro | H | 472 [M + H]+ |
| 27 | H | methyl | H | trifluoromethyl | H | fluoro | H | 456 [M + H]+ |

Example 1: N-(6-chloro-2-methoxythieno[3,2-b]pyrazin-3-yl)-4-(3,5-dimethoxyphenyl)piperazin-1-carboxamide

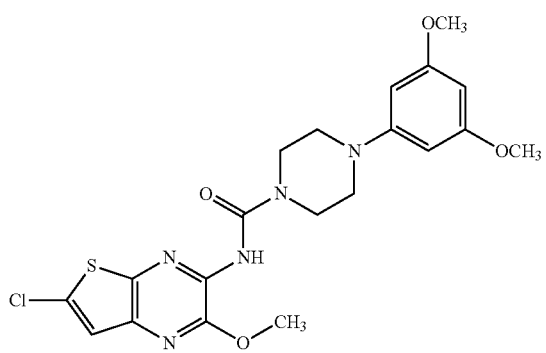 [SMILES: COc1cc(OC)cc(N2CCN(C(=O)Nc3nc4sc(Cl)cc4nc3OC)CC2)c1]

Step 1: Preparation of 5-bromo-6-chloropyrazine-2-amine 6-chloropyrazine-2-amine (10.4 g, 80 mmol) was dissolved in methanol (300 ml), and N-bromosuccinimide (15.6 g, 88 mmol) was added thereto while stirring at room temperature. After stirring for additional 60 minutes, the reaction product was concentrated under reduced pressure, followed by adding water so that the reaction product was extracted 3 times with ethyl acetate. The organic later was collected, dried over magnesium sulfate, and then concentrated under reduced pressure. Thereafter, the residue was purified on a silica gel column using chromatography. The title compound (12.0 g, 72%) was obtained by eluting as a mixed solvent (3:1 v/v) of hexane and ethyl acetate.

$^1$H NMR (500 MHz, CDCl$_3$) δ 7.69 (s, 1H), 4.73 (s, 2H).

Step 2: Preparation of 6-chloro-5-((trimethylsilyl)ethinyl)pyrazin-2-amine

Copper iodine (190 mg, 1 mmol), triethylamine (16.7 ml, 120 mmol), and [1,1'-bis(diphenylphosphino)ferrocene]dichloropalladium(II) complex with dichloromethane (1.3 g, 1.6 mmol), and tetrahydrofuran (100 ml) were added to 5-bromo-6-chloropyrazin-2-amine (4.2 g, 20 mmol) obtained from Step 1, and the resultant was bubbled using nitrogen gas. Trimethylsilylacetylene (3.6 ml, 26 mmol) was added to the mixture, and the resultant was reacted at 80° C. for 2 hours. The reactant was concentrated under reduced pressure, followed by adding water. Thereafter, the resultant was extracted 3 times with ethyl acetate. The organic layer was collected, dried over magnesium sulfate, and then concentrated under reduced pressure. Thereafter, the residue was purified on a silica gel column using chromatography. The title compound (3.16 g, 70%) was obtained by eluting as a mixed solvent (5:1 v/v) of hexane and ethyl acetate.

$^1$H NMR (500 MHz, CDCl$_3$) δ 7.84 (s, 1H), 4.85 (s, 2H), 0.28 (s, 9H).

Step 3: Preparation of thieno[3,2-b]pyrazin-3-amine 6-chloro-5-((trimethylsilyl)ethinyl)pyrazin-2-amine obtained from Step 2 was dissolved in dimethylformamide (5.0 g, 22.2 mmol). Thereafter, sodium sulfide pentahydrate (14.9 g, 88.8 mmol) was added thereto, and the resultant was stirred at 90° C. for 2 hours. After adding water, the reaction product was extracted 3 times with ethyl acetate. The organic layer was collected, dried over magnesium sulfate, and then concentrated under reduced pressure. Thereafter, the residue was purified on a silica gel column using chromatography. The title compound (3.9 g, 69%) was obtained by eluting as a mixed solvent (1:1 v/v) of hexane and ethyl acetate.

$^1$H NMR (500 MHz, CDCl$_3$) δ 8.07 (s, 1H), 7.36 (d, J=5.5 Hz, 1H), 7.32 (d, J=5.5 Hz, 1H), 4.70 (s, 2H).

Step 4: Preparation of 2,6-dichlorothieno[3,2-b]pyrazin-3-amine

Thieno[3,2-b]pyrazin-3-amine (605 mg, 4 mmol) obtained from Step 3 was dissolved in acetonitrile (60 mL). Thereafter, N-chlorosuccinimide (1.17 g, 8.8 mmol) was added thereto, and the resultant was stirred at 70° C. for 30 minutes. The resultant was concentrated under reduced pressure, followed by adding water. Thereafter, the reaction product was extracted 3 times with ethyl acetate. The organic layer was collected and dried over magnesium sulfate. After concentrating the same under reduced pressure, the produced solid was washed with diethyl ether to obtain the title compound (881 mg, 70%).

$^1$H NMR (500 MHz, CDCl$_3$) δ 7.13 (s, 1H), 5.10 (s, 2H).

Step 5: Preparation of 6-chloro-2-methoxythieno[3,2-b]pyrazin-3-amine 2,6-dichlorothieno[3,2-b]pyrazin-3-amine (819 mg, 3.8 mmol) obtained from Step 4 was dissolved in methanol (15 mL). Sodium methoxide (30 wt %; 7.06 mL, 38 mmol) was added thereto, and the resultant was stirred at 90° C. for 1 hour. The methanol was removed from the resultant, followed by adding water. Thereafter, the reaction product was extracted 3 times with ethyl acetate. The organic layer was collected, dried over magnesium sulfate, and then concentrated under reduced pressure. Thereafter, the residue was purified on a silica gel column using chromatography. The title compound (492 mg, 60%) was obtained by eluting as a mixed solvent (5:1 v/v) of hexane and ethyl acetate.

$^1$H NMR (500 MHz, CDCl$_3$) δ 7.05 (s, 1H), 4.93 (s, 2H), 4.04 (s, 3H).

Step 6: Preparation of diphenyl 6-chloro-2-methoxythieno[3,2-b]pyrazin-3-yliminodicarbonate After dissolving 6-chloro-2-methoxythieno[3,2-b]pyrazin-3-amine (43 mg, 0.2 mmol) obtained from Step 5 in tetrahydrofuran (5 mL), pyridine (0.485 mL, 6 mmol) was added thereto. Thereafter, phenyl chloroformate (0.113 mL, 0.9 mmol) was added, and the resultant was stirred at 80° C. for 1 hour. After removal of the solvent, water was added, and then the reaction product was extracted 3 times with ethyl acetate. The organic layer was collected, dried over magnesium sulfate, and then concentrated under reduced pressure. Thereafter, the residue was purified on a silica gel column using chromatography. The title compound (77.5 mg, 85%) was obtained by eluting as a mixed solvent (5:1 v/v) of hexane and ethyl acetate.

$^1$H NMR (500 MHz, CDCl$_3$) δ 7.37 (t, J=7.5 Hz, 4H), 7.31-7.21 (m, 3H), 7.15 (d, J=7.8 Hz, 4H), 4.17 (s, 3H).

Step 7: Preparation of N-(6-chloro-2-methoxythieno[3,2-b]pyrazin-3-yl)-4-(3,5-dimethoxyphenyl)piperazin-1-carboxamide After dissolving diphenyl 6-chloro-2-methoxythieno[3,2-b]pyrazin-3-yliminodicarbonate (40 mg, 0.088 mmol) obtained from Step 6 in acetonitrile, triethylamine (0.037 mL, 0.264 mmol) was added thereto. Thereafter, 1-(3,5-dimethoxyphenyl)piperazine (33 mg, 0.22 mmol) was added, and the resultant was stirred at 60° C. for 30 minutes. After concentrating the solvent under reduced pressure, the produced solid was washed with diethyl ether to obtain the title compound (37 mg, 66%).

$^1$H NMR (500 MHz, DMSO-d$_6$) δ 9.17 (s, 1H), 7.55 (s, 1H), 6.11 (d, J=1.9 Hz, 2H), 6.00 (s, 1H), 3.96 (s, 3H), 3.71 (s, 6H), 3.64-3.53 (m, 4H), 3.22-3.11 (m, 4H).

Example 2: N-(6-chloro-2-methoxythieno[3,2-b]pyrazin-3-yl)-4-(3,5-dimethylphenyl)piperazin-1-carboxamide

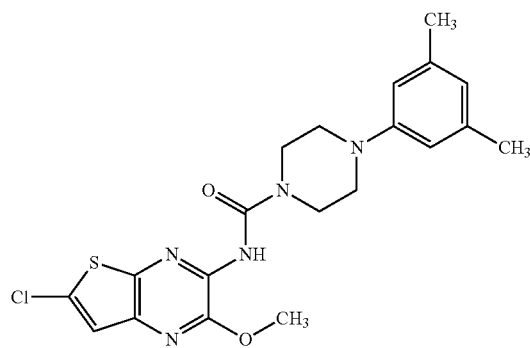 [SMILES: COc1nc2cc(Cl)sc2nc1NC(=O)N1CCN(c2cc(C)cc(C)c2)CC1]

The title compound (16 mg, 63%) was synthesized in the same manner as in Example 1, except that 1-(3,5-dimethylphenyl)piperazine was used instead of 1-(3,5-dimethoxyphenyl)piperazine in Step 7 of Example 1.

$^1$H NMR (500 MHz, DMSO-d$_6$) δ 9.16 (s, 1H), 7.55 (s, 1H), 6.59 (s, 2H), 6.46 (s, 1H), 3.96 (s, 3H), 3.64-3.51 (m, 4H), 3.19-3.07 (m, 4H), 2.21 (s, 6H).

Example 3: N-(6-chloro-2-methoxythieno[3,2-b]pyrazin-3-yl)-4-(3,5-difluorophenyl)piperazin-1-carboxamide

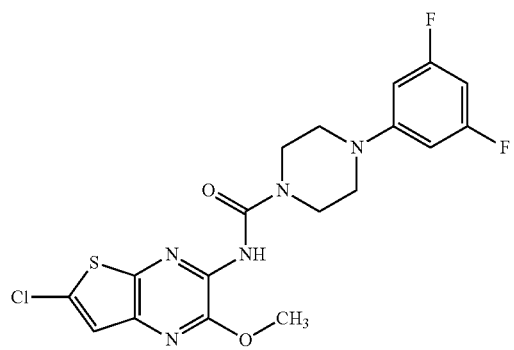 [SMILES: COc1nc2cc(Cl)sc2nc1NC(=O)N1CCN(c2cc(F)cc(F)c2)CC1]

The title compound (33 mg, 78%) was synthesized in the same manner as in Example 1, except that 1-(3,5-difluorophenyl)piperazine was used instead of 1-(3,5-dimethoxyphenyl)piperazine in Step 7 of Example 1.

$^1$H NMR (500 MHz, CDCl$_3$) δ 7.12 (d, J=7.6 Hz, 2H), 6.38 (d, J=8.7 Hz, 2H), 6.32 (t, J=8.8 Hz, 1H), 4.08 (s, 3H), 3.79-3.66 (m, 4H), 3.36-3.24 (m, 4H).

Example 4: N-(6-chloro-2-ethoxythieno[3,2-b]pyrazin-3-yl)-4-(3,5-dimethoxyphenyl)piperazin-1-carboxamide

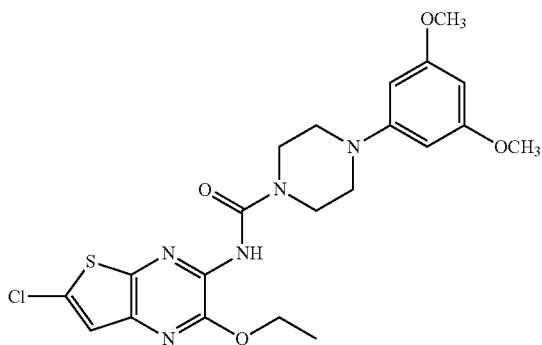 [SMILES: CCOc1nc2cc(Cl)sc2nc1NC(=O)N1CCN(c2cc(OC)cc(OC)c2)CC1]

Step 1: Preparation of 6-chloro-2-ethoxythieno[3,2-b]pyrazin-3-amine 2,6-dichlorothieno[3,2-b]pyrazin-3-amine (130 mg, 0.59 mmol) synthesized according to Steps 1 to 4 of Example 1 was dissolved in ethanol (5 mL), and then sodium ethoxide (21 wt %; 3.3 ml, 8.85 mmol) was added thereto. The resultant was stirred at 90° C. for 1 hour. The ethanol was removed from the resultant, followed by adding water. Thereafter, the reaction product was extracted 3 times with ethyl acetate. The organic layer was collected, dried over magnesium sulfate, and then concentrated under reduced pressure. Thereafter, the residue was purified on a silica gel column using chromatography. The title compound (97 mg, 70%) was obtained by eluting as a mixed solvent (5:1 v/v) of hexane and ethyl acetate.

$^1$H NMR (500 MHz, CDCl$_3$) δ 7.03 (s, 1H), 4.95 (s, 2H), 4.46 (q, J=7.1 Hz, 2H), 1.45 (t, J=7.1 Hz, 3H).

Step 2: Preparation of diphenyl 6-chloro-2-ethoxythieno[3,2-b]pyrazin-3-yliminodicarbonate After dissolving 6-chloro-2-ethoxythieno[3,2-b]pyrazin-3-amine (46 mg, 0.2 mmol) obtained from Step 1 in dichloromethane (3 mL), pyridine (0.194 mL, 2.4 mmol) was added thereto. Phenyl chloroformate (0.10 mL, 0.8 mmol) was added, and then the resultant was stirred at room temperature for 1 hour. After removal of the solvent, water was added thereto, followed by extraction with ethyl acetate 3 times. The organic layer was collected, dried over magnesium sulfate, and then concentrated under reduced pressure. Thereafter, the residue was purified on a silica gel column using chromatography. The title compound (75 mg, 80%) was obtained by eluting as a mixed solvent (10:1 v/v) of hexane and ethyl acetate.

$^1$H NMR (500 MHz, CDCl$_3$) δ 7.37 (t, J=8.0 Hz, 4H), 7.25 (dd, J=13.1, 4.8 Hz, 3H), 7.19-7.10 (m, 4H), 4.60 (q, J=7.1 Hz, 2H), 1.50 (t, J=7.1 Hz, 3H).

Step 3: Preparation of N-(6-chloro-2-ethoxythieno[3,2-b]pyrazin-3-yl)-4-(3,5-dimethoxyphenyl)piperazin-1-carboxamide After dissolving diphenyl 6-chloro-2-ethoxythieno[3,2-b]pyrazin-3-yliminodicarbonate (12 mg, 0.025 mmol) obtained from Step 2 in acetonitrile (3 mL), triethylamine (0.01 mL, 0.075 mmol) was added thereto. 1-(3,5-dimethoxyphenyl)piperazine (12 mg, 0.055 mmol) was added, and then the resultant was stirred at 60° C. for 30 minutes. After concentrating the solvent under reduced pressure, the produced solid was washed with a mixed solvent (10:1 v/v) of hexane and diethyl ether to obtain the title compound (7 mg, 59%).

$^1$H NMR (500 MHz, CDCl$_3$) δ 7.12 (s, 1H), 7.10 (s, 1H), 6.10 (d, J=2.0 Hz, 2H), 6.07 (t, J=1.9 Hz, 1H), 4.51 (q, J=7.1 Hz, 2H), 3.79 (s, 6H), 3.76-3.68 (m, 4H), 3.31-3.23 (m, 4H), 1.47 (t, J=7.1 Hz, 3H).

Example 5: N-(6-chloro-2-ethoxythieno[3,2-b]pyrazin-3-yl)-4-(3,5-dimethylphenyl)piperazin-1-carboxamide

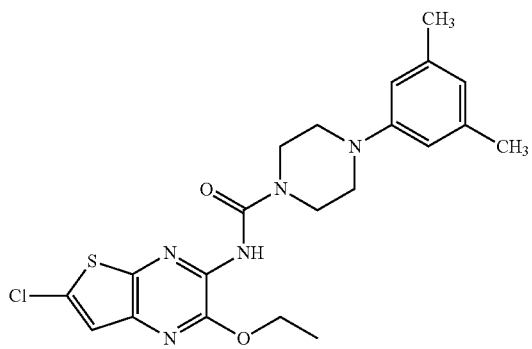 [SMILES: CCOc1nc2cc(Cl)sc2nc1NC(=O)N1CCN(c2cc(C)cc(C)c2)CC1]

The title compound (8 mg, 70%) was synthesized in the same manner as in Example 4, except that 1-(3,5-dimethylphenyl)piperazine was used instead of 1-(3,5-dimethoxyphenyl)piperazine in Step 3 of Example 4.

$^1$H NMR (500 MHz, CDCl$_3$) δ 7.12 (s, 1H), 7.10 (s, 1H), 6.58 (s, 3H), 4.51 (q, J=7.1 Hz, 2H), 3.79-3.66 (m, 4H), 3.31-3.20 (m, 4H), 2.30 (s, 6H), 1.47 (t, J=7.1 Hz, 3H).

Example 6: N-(6-chloro-2-ethoxythieno[3,2-b]pyrazin-3-yl)-4-(3,5-difluorophenyl)piperazin-1-carboxamide

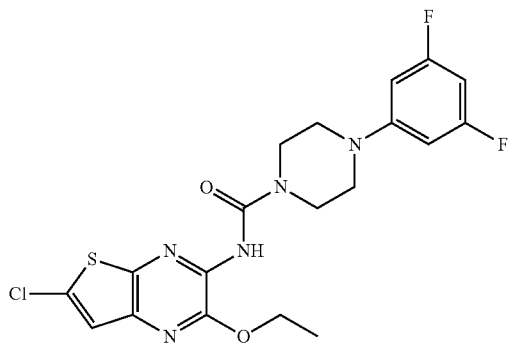 [SMILES: CCOc1nc2cc(Cl)sc2nc1NC(=O)N1CCN(c2cc(F)cc(F)c2)CC1]

The title compound (10 mg, 69%) was synthesized in the same manner as in Example 4, except that 1-(3,5-difluorophenyl)piperazine was used instead of 1-(3,5-dimethoxyphenyl)piperazine in Step 3 of Example 4.

$^1$H NMR (500 MHz, CDCl$_3$) δ 7.16-7.08 (m, 2H), 6.38 (dd, J=10.2, 1.9 Hz, 2H), 6.35-6.28 (m, 1H), 4.51 (dt, J=10.1, 5.6 Hz, 2H), 3.81-3.65 (m, 4H), 3.36-3.25 (m, 4H), 1.48 (td, J=7.0, 2.5 Hz, 3H).

Example 7: N-(6-chloro-2-isopropoxythieno[3,2-b]pyrazin-3-yl)-4-(3,5-dimethoxyphenyl)piperazin-1-carboxamide

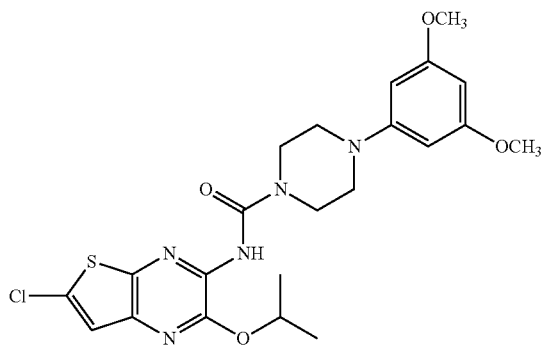 [SMILES: COc1cc(OC)cc(N2CCN(C(=O)Nc3nc4sc(Cl)cc4nc3OC(C)C)CC2)c1]

The title compound (12 mg, 68%) was synthesized in the same manner as in Example 4, except that in Step 3 of Example 4, diphenyl 6-chloro-2-isopropoxythieno[3,2-b]pyrazin-3-yliminodicarbonate, instead of diphenyl 6-chloro-2-ethoxythieno[3,2-b]pyrazin-3-yliminodicarbonate, was reacted with 1-(3,5-dimethoxyphenyl)piperazine.

$^1$H NMR (500 MHz, CDCl$_3$) δ 7.05 (s, 1H), 6.08 (s, 1H), 6.00 (d, J=2.0 Hz, 2H), 5.97 (t, J=1.9 Hz, 1H), 4.31 (q, J=7.1 Hz, 2H), 4.12 (sep, J=5.3 Hz, 1H), 3.72 (s, 6H), 3.52-3.32 (m, 4H), 3.11-3.02 (m, 4H), 1.47 (d, J=5.3 Hz, 6H).

Example 8: N-(6-chloro-2-isopropoxythieno[3,2-b]pyrazin-3-yl)-4-(3,5-dimethylphenyl)piperazin-1-carboxamide

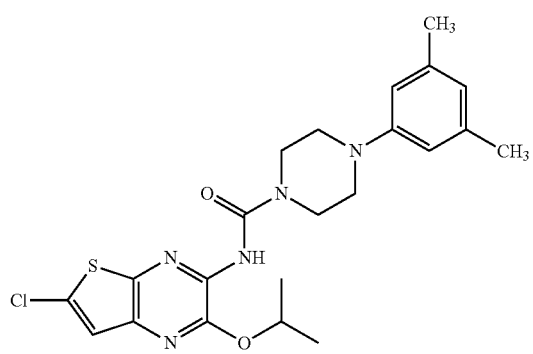 [SMILES: Cc1cc(C)cc(N2CCN(C(=O)Nc3nc4sc(Cl)cc4nc3OC(C)C)CC2)c1]

The title compound (15 mg, 75%) was synthesized in the same manner as in Example 7, except that in Example 7, diphenyl 6-chloro-2-isopropoxythieno[3,2-b]pyrazin-3-yliminodicarbonate was reacted with 1-(3,5-dimethylphenyl)piperazine instead of 1-(3,5-dimethoxyphenyl)piperazine.

$^1$H NMR (500 MHz, CDCl$_3$) δ 7.08 (s, 1H), 7.02 (s, 1H), 6.43 (s, 3H), 4.07 (sep, J=5.4 Hz, 1H), 3.68-3.56 (m, 4H), 3.30-3.20 (m, 4H), 2.29 (s, 6H), 1.46 (d, J=5.4 Hz, 6H).

Example 9: N-(6-chloro-2-isopropoxythieno[3,2-b]pyrazin-3-yl)-4-(3,5-difluorophenyl)piperazin-1-carboxamide

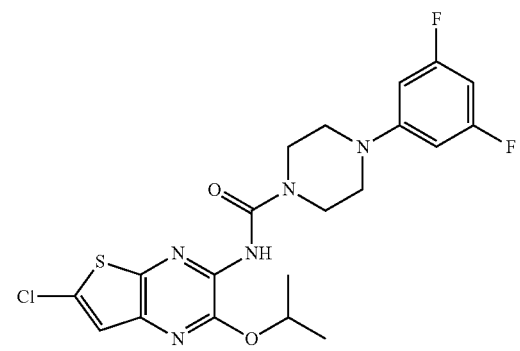 [SMILES: CC(C)Oc1nc2cc(Cl)sc2nc1NC(=O)N1CCN(c2cc(F)cc(F)c2)CC1]

The title compound (13 mg, 71%) was synthesized in the same manner as in Example 7, except that in Example 7, diphenyl 6-chloro-2-isopropoxythieno[3,2-b]pyrazin-3-yliminodicarbonate was reacted with 1-(3,5-difluorophenyl)piperazine instead of 1-(3,5-dimethoxyphenyl)piperazine.

Example 10: 4-(3,5-dimethoxyphenyl)-N-(2-methoxythieno[3,2-b]pyrazin-3-yl)piperazin-1-carboxamide

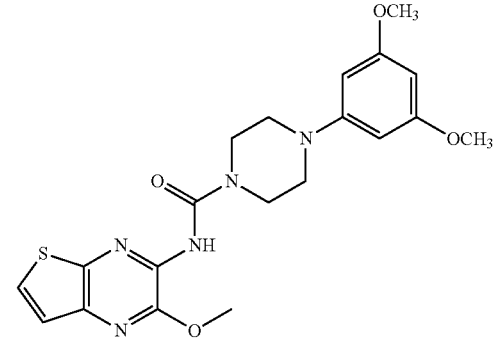 [SMILES: COc1cc(OC)cc(N2CCN(C(=O)Nc3nc4sccc4nc3OC)CC2)c1]

Step 1: Preparation of 2-methoxythieno[3,2-b]pyrazin-3-amine

After dissolving 6-chloro-2-methoxythieno[3,2-b]pyrazin-3-amine (431 mg, 2 mmol) synthesized according to Steps 1 to 5 of Example 1 in ethanol (15 mL), palladium charcoal (851 mg, 2 mmol), and ammonium formate (1.51 g, 24 mmol) were added thereto. The resultant was then reacted at 100° C. for 30 minutes using a microwave reactor. After filtering the reaction solution with Celite, the solvent was removed therefrom, and then water was added to extract with ethyl acetate. The organic layer was collected, dried over magnesium sulfate, and then concentrated under reduced pressure. Thereafter, the residue was purified on a silica gel column using chromatography. The title compound (315 mg, 87%) was obtained by eluting as a mixed solvent (5:1 v/v) of hexane and ethyl acetate.

$^1$H NMR (500 MHz, CDCl$_3$) δ 7.24 (d, J=5.9 Hz, 1H), 7.19 (d, J=5.9 Hz, 1H), 5.01 (s, 2H), 4.06 (s, 3H).

Step 2: Preparation of diphenyl 2-methoxythieno[3,2-b]pyrazin-3-yliminodicarbonate After dissolving 2-methoxythieno[3,2-b]pyrazin-3-amine obtained from Step 1 in dichloromethane, pyridine was added thereto. Phenyl chloroformate was additionally added, and then the resultant was stirred at room temperature for 1 hour. After removal of the solvent, water was added, and then the reaction product was extracted 3 times with ethyl acetate. The organic layer was collected, dried over magnesium sulfate, and then concentrated under reduced pressure. Thereafter, the residue was purified on a silica gel column using chromatography. The title compound (2.3 g, 73%) was obtained by eluting as a mixed solvent (7:1 v/v) of hexane and ethyl acetate.

$^1$H NMR (500 MHz, CDCl$_3$) δ 7.88 (d, J=6.0 Hz, 1H), 7.41 (d, J=6.0 Hz, 1H), 7.36 (t, J=7.9 Hz, 4H), 7.24 (dd, J=10.9, 4.0 Hz, 2H), 7.15 (d, J=8.4 Hz, 4H), 4.19 (s, 3H).

Step 3: Preparation of 4-(3,5-dimethoxyphenyl)-N-(2-methoxythieno[3,2-b]pyrazin-3-yl)piperazin-1-carboxamide After dissolving diphenyl 2-methoxythieno[3,2-b]pyrazin-3-yliminodicarbonate obtained from Step 2 in acetonitrile, triethylamine was added thereto. 1-(3,5-dimethoxyphenyl)piperazine was added, and the resultant was stirred at 60° C. for 30 minutes. After concentrating the solvent under reduced pressure, the produced solid was washed with diethyl ether to obtain the title compound (470 mg, 78%).

$^1$H NMR (500 MHz, CDCl$_3$) δ 7.49 (d, J=5.9 Hz, 1H), 7.26 (d, J=2.3 Hz, 1H), 7.13 (s, 1H), 6.11 (d, J=1.8 Hz, 2H), 6.07 (s, 1H), 4.10 (s, 3H), 3.79 (s, 6H), 3.76-3.69 (m, 4H), 3.32-3.21 (m, 4H).

Example 11: 4-(3,5-dimethylphenyl)-N-(2-methoxythieno[3,2-b]pyrazin-3-yl)piperazin-1-carboxamide

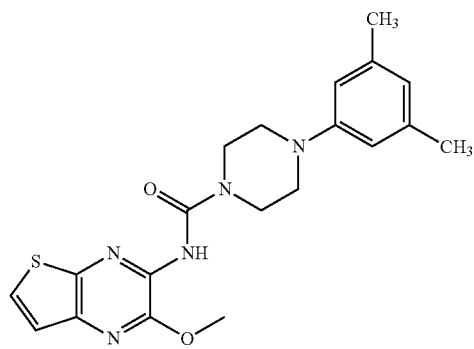 [SMILES: COc1nc2ccsc2nc1NC(=O)N1CCN(c2cc(C)cc(C)c2)CC1]

The title compound (450 mg, 87%) was synthesized in the same manner as in Example 10, except that 1-(3,5-dimethylphenyl)piperazine was used instead of 1-(3,5-dimethoxyphenyl)piperazine in Step 3 of Example 10.

$^1$H NMR (500 MHz, CDCl$_3$) δ 7.48 (d, J=5.9 Hz, 1H), 7.25 (d, J=6.2 Hz, 1H), 7.11 (s, 1H), 6.58 (s, 3H), 4.10 (s, 3H), 3.81-3.68 (m, 4H), 3.34-3.22 (m, 4H), 2.29 (s, 6H).

Example 12: 4-(3,5-difluorophenyl)-N-(2-methoxythieno[3,2-b]pyrazin-3-yl)piperazin-carboxamide-1

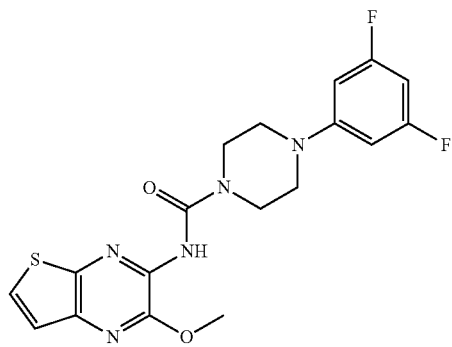 [SMILES: COc1nc2ccsc2nc1NC(=O)N1CCN(c2cc(F)cc(F)c2)CC1]

The title compound (505 mg, 95%) was synthesized in the same manner as in Example 10, except that 1-(3,5-difluorophenyl)piperazine was used instead of 1-(3,5-dimethoxyphenyl)piperazine in Step 3 of Example 10.

$^1$H NMR (500 MHz, CDCl$_3$) δ 7.50 (d, J=5.9 Hz, 1H), 7.27-7.25 (m, 1H), 7.13 (s, 1H), 6.38 (dd, J=10.2, 1.8 Hz, 2H), 6.31 (ddd, J=8.8, 5.5, 2.1 Hz, 1H), 4.10 (s, 3H), 3.77-3.70 (m, 4H), 3.35-3.26 (m, 4H).

Example 13: 4-(3,5-dimethoxyphenyl)-N-(2-ethoxythieno[3,2-b]pyrazin-3-yl)piperazin-1-carboxamide

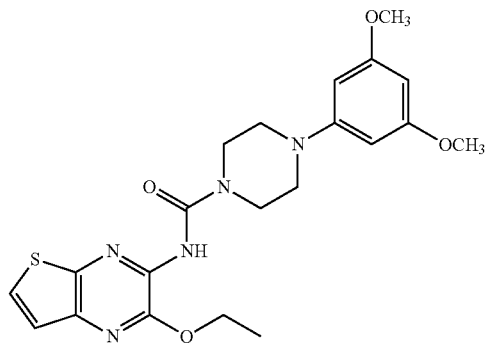 [SMILES: CCOc1nc2ccsc2nc1NC(=O)N1CCN(c2cc(OC)cc(OC)c2)CC1]

Step 1: Preparation of 2-ethoxythieno[3,2-b]pyrazin-3-amine

After dissolving 6-chloro-2-ethoxythieno[3,2-b]pyrazin-3-amine synthesized according to Step 1 of Example 4 in ethanol, palladium charcoal and ammonium formate were added thereto. The resultant was then reacted at 100° C. for 30 minutes using a microwave reactor. After filtering the reaction solution with Celite, the solvent was removed therefrom, and then water was added to extract with ethyl acetate. The organic layer was collected, dried over magnesium sulfate, and then concentrated under reduced pressure. Thereafter, the residue was purified on a silica gel column using chromatography. The title compound (45 mg, 70%) was obtained by eluting as a mixed solvent (5:1 v/v) of hexane and ethyl acetate.

¹H NMR (500 MHz, CDCl₃) δ 7.23 (d, J=5.9 Hz, 1H), 7.17 (d, J=5.9 Hz, 1H), 4.98 (s, 2H), 4.50 (q, J=7.1 Hz, 2H), 1.46 (t, J=7.1 Hz, 3H).

Step 2: Preparation of diphenyl 2-ethoxythieno[3,2-b]pyrazin-3-yliminodicarbonate After dissolving 2-ethoxythieno[3,2-b]pyrazin-3-amine obtained from Step 1 in dichloromethane, pyridine was added thereto. Phenyl chloroformate was additionally added, and then the resultant was stirred at room temperature for 1 hour. After removal of the solvent, water was added, and then the reaction product was extracted 3 times with ethyl acetate. The organic layer was collected, dried over magnesium sulfate, and then concentrated under reduced pressure. Thereafter, the residue was purified on a silica gel column using chromatography. The title compound (85 mg, 97%) was obtained by eluting as a mixed solvent (10:1 v/v) of hexane and ethyl acetate.

¹H NMR (500 MHz, CDCl₃) δ 7.87 (d, J=6.0 Hz, 1H), 7.37 (dd, J=15.0, 7.1 Hz, 5H), 7.24 (dd, J=13.7, 6.3 Hz, 3H), 7.15 (d, J=8.2 Hz, 4H), 4.63 (q, J=7.1 Hz, 2H), 1.51 (t, J=7.1 Hz, 3H).

Step 3: Preparation of 4-(3,5-dimethoxyphenyl)-N-(2-ethoxythieno[3,2-b]pyrazin-3-yl)piperazin-1-carboxamide After dissolving diphenyl 2-ethoxythieno[3,2-b]pyrazin-3-yliminodicarbonate (18.7 mg, 0.043 mmol) obtained from Step 2 in acetonitrile (3 ml), triethylamine (0.024 ml, 0.172 mmol) was added thereto. 1-(3,5-dimethoxyphenyl)piperazine (32 mg, 0.096 mmol) was added, and then the resultant was stirred at 60° C. for 30 minutes. The residue obtained by concentrating the solvent under reduced pressure was purified on a silica gel column using chromatography. The title compound (15 mg, 78%) was obtained by eluting as a mixed solvent (1:1 v/v) of hexane and ethyl acetate.

¹H NMR (500 MHz, CDCl₃) δ 7.47 (d, J=5.9 Hz, 1H), 7.23 (d, J=5.9 Hz, 1H), 7.13 (s, 1H), 6.11 (d, J=2.0 Hz, 2H), 6.06 (t, J=2.0 Hz, 1H), 4.53 (q, J=7.1 Hz, 2H), 3.79 (s, 6H), 3.76-3.70 (m, 4H), 3.33-3.19 (m, 4H), 1.48 (t, J=7.1 Hz, 3H).

Example 14: 4-(3,5-dimethylphenyl)-N-(2-ethoxythieno[3,2-b]pyrazin-3-carboxamide-yl)piperazin-1

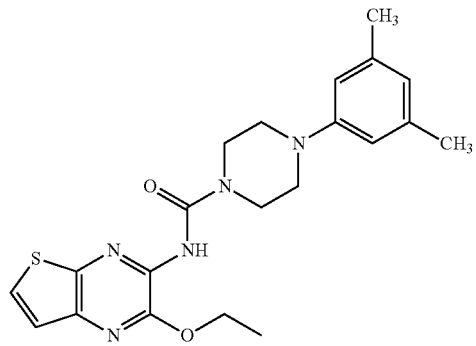 [SMILES: CCOc1nc2ccsc2nc1NC(=O)N1CCN(c2cc(C)cc(C)c2)CC1]

The title compound (13 mg, 71%) was synthesized in the same manner as in Example 13, except that 1-(3,5-dimethylphenyl)piperazine was used instead of 1-(3,5-dimethoxyphenyl)piperazine in Step 3 of Example 13.

¹H NMR (500 MHz, CDCl₃) δ 7.47 (d, J=5.8 Hz, 1H), 7.23 (d, J=5.9 Hz, 1H), 7.14 (s, 1H), 6.58 (s, 3H), 4.54 (q, J=6.9 Hz, 2H), 3.79-3.67 (m, 4H), 3.35-3.21 (m, 4H), 2.29 (s, 6H), 1.48 (t, J=7.0 Hz, 3H).

Example 15: 4-(3,5-difluorophenyl)-N-(2-ethoxythieno[3,2-b]pyrazin-3-yl)piperazin-1-carboxamide

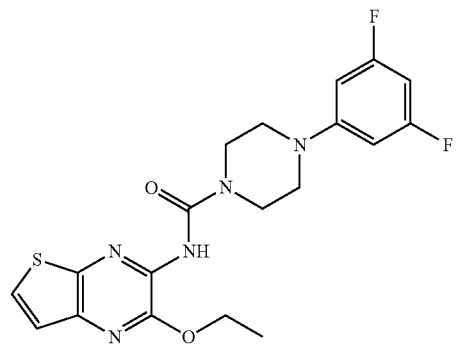 [SMILES: CCOc1nc2ccsc2nc1NC(=O)N1CCN(c2cc(F)cc(F)c2)CC1]

The title compound (9 mg, 47%) was synthesized in the same manner as in Example 13, except that 1-(3,5-difluorophenyl)piperazine was used instead of 1-(3,5-dimethoxyphenyl)piperazine in Step 3 of Example 13.

¹H NMR (500 MHz, CDCl₃) δ 7.48 (d, J=5.9 Hz, 1H), 7.24 (d, J=5.9 Hz, 1H), 7.13 (s, 1H), 6.38 (d, J=8.4 Hz, 2H), 6.31 (dd, J=9.8, 7.8 Hz, 1H), 4.54 (q, J=7.1 Hz, 2H), 3.81-3.66 (m, 4H), 3.36-3.26 (m, 4H), 1.49 (t, J=7.1 Hz, 3H).

Example 16: 4-(3,5-dimethoxyphenyl)-N-(2-isopropoxythieno[3,2-b]pyrazin-3-yl)piperazin-1-carboxamide

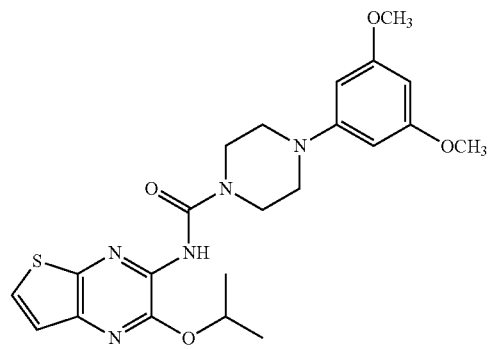 [SMILES: COc1cc(OC)cc(N2CCN(C(=O)Nc3nc4sccc4nc3OC(C)C)CC2)c1]

The title compound (16 mg, 69%) was synthesized in the same manner as in Example 13, except that in Step 3 of Example 13, diphenyl 2-isopropoxythieno[3,2-b]pyrazin-3-yliminodicarbonate, instead of diphenyl 2-ethoxythieno[3,2-b]pyrazin-3-yliminodicarbonate, was reacted with 1-(3,5-dimethoxyphenyl)piperazine.

¹H NMR (500 MHz, CDCl₃) δ 7.37 (d, J=5.9 Hz, 1H), 7.12 (d, J=2.3 Hz, 1H), 7.05 (s, 1H), 6.06 (d, J=1.8 Hz, 2H), 6.01 (s, 1H), 4.02 (sep, J=5.5 Hz, 1H), 3.69 (s, 6H), 3.55-3.32 (m, 4H), 3.20-3.05 (m, 4H), 1.42 (d, J=5.5 Hz, 6H).

Example 17: 4-(3,5-dimethylphenyl)-N-(2-isopropoxythieno[3,2-b]pyrazin-3-yl)piperazin-1-carboxamide

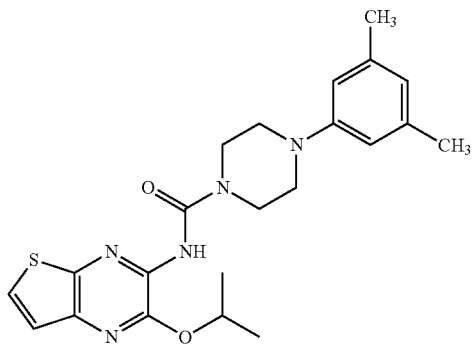 [SMILES: Cc1cc(C)cc(N2CCN(C(=O)Nc3nc4sccc4nc3OC(C)C)CC2)c1]

The title compound (11 mg, 74%) was synthesized in the same manner as in Example 16, except that in Example 16, diphenyl 2-isopropoxythieno[3,2-b]pyrazin-3-yliminodicarbonate was reacted with 1-(3,5-dimethylphenyl)piperazine instead of 1-(3,5-dimethoxyphenyl)piperazine.

$^1$H NMR (500 MHz, CDCl$_3$) δ 7.44 (d, J=5.8 Hz, 1H), 7.21 (d, J=5.9 Hz, 1H), 7.12 (s, 1H), 6.54 (s, 3H), 3.99 (sep, J=5.5 Hz, 1H), 3.70-3.59 (m, 4H), 3.31-3.16 (m, 4H), 2.21 (s, 6H), 1.40 (d, J=5.5 Hz, 6H).

Example 18: 4-(3,5-difluorophenyl)-N-(2-isopropoxythieno[3,2-b]pyrazin-3-yl)piperazin-1-carboxamide

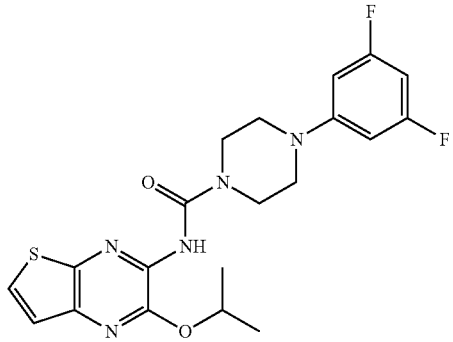 [SMILES: CC(C)Oc1nc2ccsc2nc1NC(=O)N1CCN(c2cc(F)cc(F)c2)CC1]

The title compound (10 mg, 71%) was synthesized in the same manner as in Example 16, except that in Example 16, diphenyl 2-isopropoxythieno[3,2-b]pyrazin-3-yliminodicarbonate was reacted with 1-(3,5-difluorophenyl)piperazine instead of 1-(3,5-dimethoxyphenyl)piperazine.

$^1$H NMR (500 MHz, CDCl$_3$) δ 7.48 (d, J=5.9 Hz, 1H), 7.22 (d, J=5.9 Hz, 1H), 7.12 (s, 1H), 6.31 (d, J=8.4 Hz, 2H), 6.28 (dd, J=9.8, 7.8 Hz, 1H), 4.09 (sep, J=5.1 Hz, 1H), 3.78-3.59 (m, 4H), 3.28-3.18 (m, 4H), 1.52 (d, J=5.1 Hz, 6H).

Example 19: N-(2-methoxythieno[3,2-b]pyrazin-3-yl)-4-(3-methyl-5-(trifluoromethoxy)phenyl)piperazin-1-carboxamide

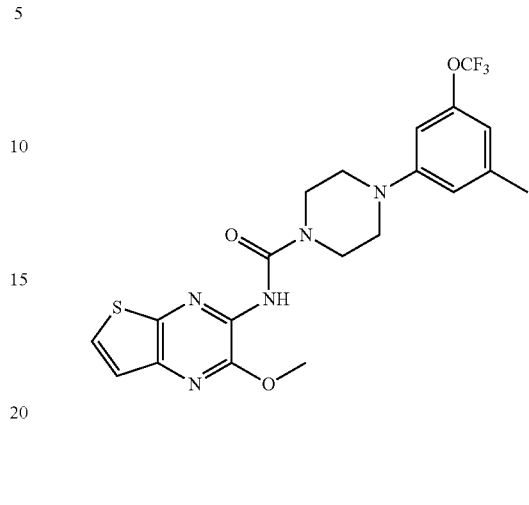

Phenyl N-(2-methoxythieno[3,2-b]pyrazin-3-yl)-N-phenoxycarbonyl carbamate and 1-(3-methyl-5-(trifluoromethoxy)phenyl)piperazine were reacted in the same manner as in Step 3 of Example 10 to synthesize the title compound (85 mg, 94%).

$^1$H NMR (500 MHz, CDCl$_3$) δ 7.49 (d, J=5.9 Hz, 1H), 7.26 (d, J=5.7 Hz, 1H), 7.13 (s, 1H), 6.35-6.52 (m, 3H), 4.10 (s, 3H), 3.76-3.70 (m, 4H), 3.30-3.22 (m, 4H), 2.41 (s, 3H).

Example 20: N-(2-methoxythieno[3,2-b]pyrazin-3-yl)-4-(3-(trifluoromethoxy)-5-(trifluoromethyl)phenyl)piperazin-1-carboxamide

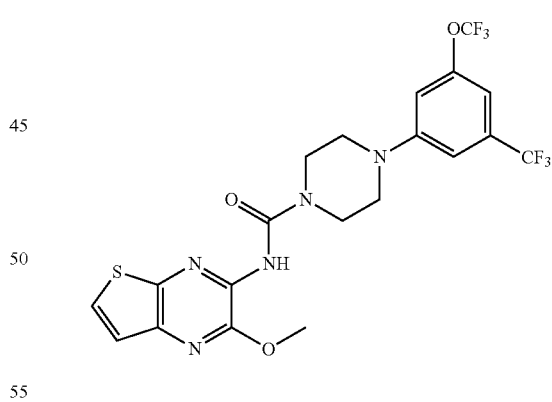

Phenyl N-(2-methoxythieno[3,2-b]pyrazin-3-yl)-N-phenoxycarbonyl carbamate and 1-(3-(trifluoromethoxy)-5-(trifluoromethyl)phenyl)piperazine were reacted in the same manner as in Step 3 of Example 10 to synthesize the title compound (112 mg, 91%).

$^1$H NMR (500 MHz, CDCl$_3$) δ 7.47 (d, J=5.9 Hz, 1H), 7.25 (d, J=5.7 Hz, 1H), 7.13 (s, 1H), 6.15-6.32 (m, 3H), 4.20 (s, 3H), 3.76-3.70 (m, 4H), 3.30-3.22 (m, 4H).

Example 21: 4-(3-methoxy-5-methylphenyl)-N-(2-methoxythieno[3,2-b]pyrazin-3-yl)piperazin-1-carboxamide

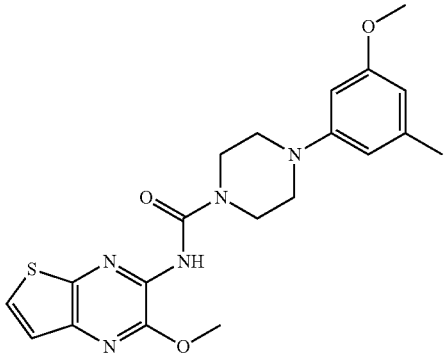 [SMILES: COc1cc(C)cc(N2CCN(C(=O)Nc3nc4sccc4nc3OC)CC2)c1]

Phenyl N-(2-methoxythieno[3,2-b]pyrazin-3-yl)-N-phenoxycarbonyl carbamate and 1-(3-methoxy-5-methylphenyl)piperazine were reacted in the same manner as in Step 3 of Example 10 to synthesize the title compound (90 mg, 92%).

$^1$H NMR (500 MHz, CDCl$_3$) δ 7.43 (d, J=5.9 Hz, 1H), 7.26 (d, J=5.7 Hz, 1H), 7.12 (s, 1H), 6.41 (s, 1H), 6.32 (s, 2H), 4.10 (s, 3H), 3.82 (s, 3H), 3.76-3.70 (m, 4H), 3.30-3.22 (m, 4H), 2.32 (s, 3H).

Example 22: 4-(3-fluoro-5-methoxyphenyl)-N-(2-methoxythieno[3,2-b]pyrazin-3-yl)piperazin-1-carboxamide

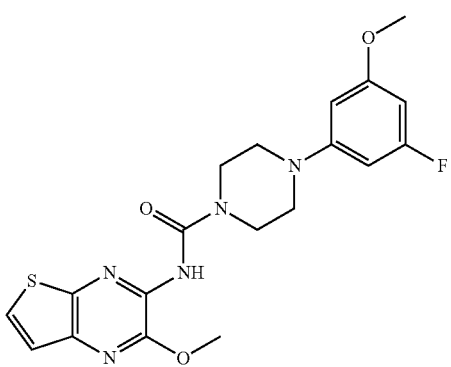 [SMILES: COc1cc(F)cc(N2CCN(C(=O)Nc3nc4sccc4nc3OC)CC2)c1]

Phenyl N-(2-methoxythieno[3,2-b]pyrazin-3-yl)-N-phenoxycarbonyl carbamate and 1-(3-fluoro-5-methoxyphenyl)piperazine were reacted in the same manner as in Step 3 of Example 10 to synthesize the title compound (89 mg, 90%).

$^1$H NMR (500 MHz, CDCl$_3$) δ 7.42 (d, J=5.9 Hz, 1H), 7.26 (d, J=5.7 Hz, 1H), 7.11 (s, 1H), 6.23-6.55 (m, 3H), 4.10 (s, 3H), 3.85 (s, 3H), 3.76-3.70 (m, 4H), 3.30-3.22 (m, 4H).

Example 23: 4-(3-fluoro-5-methylphenyl)-N-(2-methoxythieno[3,2-b]pyrazin-3-yl)piperazin-1-carboxamide

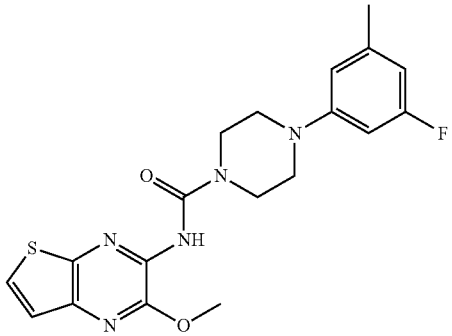 [SMILES: COc1nc2ccsc2nc1NC(=O)N1CCN(c2cc(C)cc(F)c2)CC1]

Phenyl N-(2-methoxythieno[3,2-b]pyrazin-3-yl)-N-phenoxycarbonyl carbamate and 1-(3-fluoro-5-methylphenyl)piperazine were reacted in the same manner as in Step 3 of Example 10 to synthesize the title compound (95 mg, 95%).

$^1$H NMR (500 MHz, CDCl$_3$) δ 7.47 (d, J=5.9 Hz, 1H), 7.22 (d, J=5.7 Hz, 1H), 7.13 (s, 1H), 6.21-6.45 (m, 3H), 4.13 (s, 3H), 3.76-3.70 (m, 4H), 3.30-3.22 (m, 4H), 2.23 (s, 3H).

Example 24: N-(2-methoxythieno[3,2-b]pyrazin-3-yl)-4-(3-(trifluoromethoxy)phenyl)piperazin-1-carboxamide

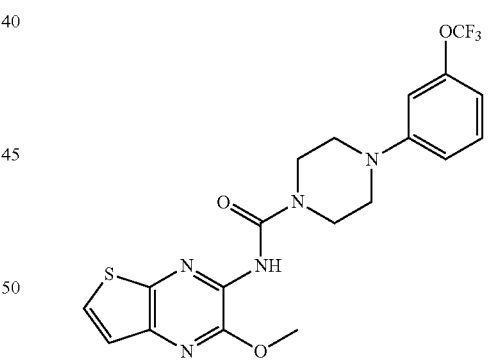

Phenyl N-(2-methoxythieno[3,2-b]pyrazin-3-yl)-N-phenoxycarbonyl carbamate and 1-(3-(trifluoromethoxy)phenyl)piperazine were reacted in the same manner as in Step 3 of Example 10 to synthesize the title compound (103 mg, 96%).

$^1$H NMR (500 MHz, CDCl$_3$) δ 7.45 (d, J=5.9 Hz, 1H), 7.23 (d, J=5.7 Hz, 1H), 7.12 (s, 1H), 6.92 (s, 1H), 6.81-6.86 (d, J=8.2 Hz, 1H), 6.76 (d, J=9.0 Hz, 2H), 4.11 (s, 3H), 3.76-3.70 (m, 4H), 3.30 J 3.22 (m, 4H).

Example 25: 4-(3-methoxy-5-(trifluoromethoxy)phenyl)-N-(2-methoxythieno[3,2-b]pyrazin-3-yl)piperazin-1-carboxamide

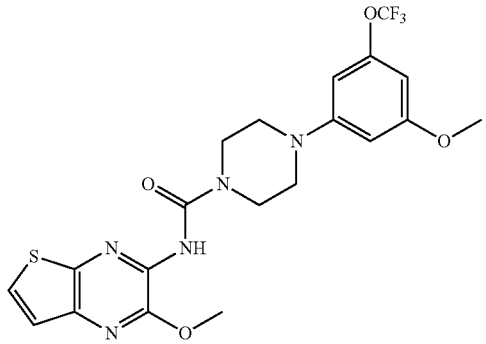 [SMILES: COc1cc(OC(F)(F)F)cc(N2CCN(C(=O)Nc3nc4sccc4nc3OC)CC2)c1]

Phenyl N-(2-methoxythieno[3,2-b]pyrazin-3-yl)-N-phenoxycarbonyl carbamate and 1-(3-methoxy-5-(trifluoromethoxy)phenyl)piperazine were reacted in the same manner as in Step 3 of Example 10 to synthesize the title compound (104 mg, 91%).

$^1$H NMR (500 MHz, CDCl$_3$) δ 7.49 (d, J=5.9 Hz, 1H), 7.26 (d, J=5.7 Hz, 1H), 7.14 (s, 1H), 6.21-6.55 (m, 3H), 4.10 (s, 3H), 3.86 (s, 3H), 3.76-3.70 (m, 4H), 3.30-3.22 (m, 4H).

Example 26: 4-(3-fluoro-5-(trifluoromethoxy)phenyl)-N-(2-methoxythieno[3,2-b]pyrazin-3-yl)piperazin-1-carboxamide

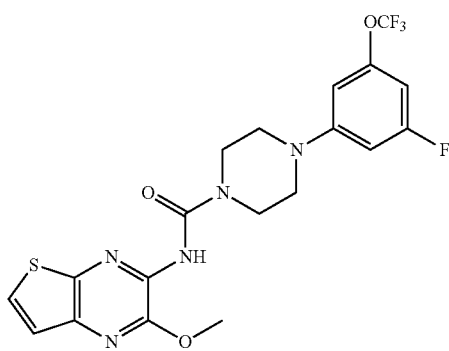 [SMILES: COc1nc2ccsc2nc1NC(=O)N1CCN(c2cc(F)cc(OC(F)(F)F)c2)CC1]

Phenyl N-(2-methoxythieno[3,2-b]pyrazin-3-yl)-N-(phenoxycarbonyl)carbamate and 1-(3-fluoro-5-(trifluoromethoxy)phenyl)piperazine were reacted in the same manner as in Step 3 of Example 10 to synthesize the title compound (100 mg, 90%).

$^1$H NMR (500 MHz, CDCl$_3$) δ 7.50 (d, J=5.9 Hz, 1H), 7.28 (d, J=5.7 Hz, 1H), 7.10 (s, 1H), 6.37-6.55 (m, 3H), 4.11 (s, 3H), 3.76-3.70 (m, 4H), 3.30-3.22 (m, 4H).

Example 27: 4-(3-fluoro-5-(trifluoromethyl)phenyl)-N-(2-methoxythieno[3,2-b]pyrazin-3-yl)piperazin-1-carboxamide

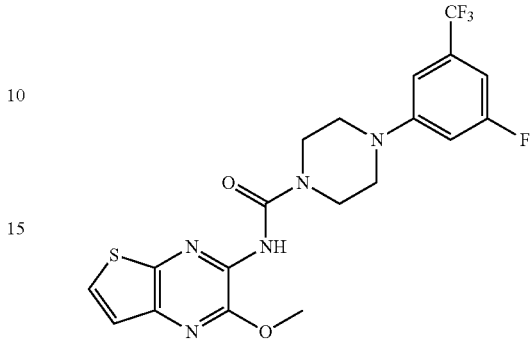

Phenyl N-(2-methoxythieno[3,2-b]pyrazin-3-yl)-N-(phenoxycarbonyl)carbamate and 1-(3-fluoro-5-(trifluoromethyl)phenyl)piperazine were reacted in the same manner as in Step 3 of Example 10 to synthesize the title compound (99 mg, 92%).

$^1$H NMR (500 MHz, CDCl$_3$) δ 7.53 (d, J=5.9 Hz, 1H), 7.30 (d, J=5.7 Hz, 1H), 7.13 (s, 1H), 6.80-6.89 (m, 2H), 6.71 (t, J=9.9 Hz, 1H), 4.11 (s, 3H), 3.76-3.70 (m, 4H), 3.30-3.22 (m, 4H).

Experimental Example 1: Culture of Cancer Cell Line

The cell lines below were used in order to confirm the efficacy of the compounds synthesized in Examples 1 to 27. Human PANC-1 (pancreatic cancer) and MDA-MB-231 (breast cancer) cell lines were obtained from American Type Culture Collection (ATCC; Manassas, Va.); and HN31 (head and neck cancer) and UMRC2 (kidney cancer) cell lines were secured from the United States National Institutes of Health (Bethesda, Md.). The MDA-MB-231, UMRC2, HN31, and PANC-1 cell lines were cultured in Dulbecco modified Eagle medium (DMEM) containing FBS (10%), HEPES (10 mM), penicillin (100 U/mL), and streptomycin (100 μg/mL). All cell lines were cultured in an incubator (37° C., 5% CO$_2$).

Experimental Example 2: Cell Growth Inhibition Experiment on Cell Line

The 4-(aryl)-N-(2-alkoxythieno[3,2-b]pyrazin-3-yl)-piperazin-1-carboxamide derivative compounds synthesized according to Examples 1 to 27 of the present invention were treated with various human tissue-derived cancer cell lines cultured according to Experimental Example 1, and thus the inhibitory effect of the growth of human cancer cells was confirmed. The cell growth inhibition experiment was conducted using sulforhodamine B (SRB) technique (Skehan et al., J. National Cancer Institute, 1990, 82: 1107-1112). Specifically, each cell line was seeded in a 96-well plate at a density of 2 to 3×10$^3$ cells/well, cultured overnight, and then treated with the 4-(aryl)-N-(2-alkoxythieno[3,2-b]pyrazin-3-yl)-piperazin-1-carboxamide derivative compounds of the present invention. The experiment was repeated 3 times for each compound. Cells treated with each compound were additionally incubated for 96 hours, fixed with 10% trichloroacetic acid (TCA), and then left at 4° C. for 1 hour. The resultant was washed 3 times with distilled water. Thereafter, each cell was treated with 0.4% sulforhodamine B dissolved in 1% acetic acid, stained for 30 minutes, and then washed 4 times with 1% acetic acid. The resultant was dried in the air. After shaking the resultant in Tris solution (10 mM) for 5 minutes, the absorbance was measured at 530 nm using a Benchmark Plus Microplate reader (Bio-Rad Laboratories, Hercules, Calif.).

In order to convert the $OD_{530}$ value to the number of viable cells per each well, the measured $OD_{530}$ value was compared to the standard $OD_{530}$-vs.-cell number curve of each cell line. The percent survival was calculated using the following formula:

$$\% \text{ survival} = N_{live\ cells}(\text{test}) / N_{live\ cells}(\text{control}) \times 100$$

$IC_{50}$ values were calculated by nonlinear regression analysis.

The $IC_{50}$ values for the compounds of Examples 1 to 27, listed in Table 1 above, were derived and are summarized in Table 2 below, which confirmed the possibility of using the compounds as anti-proliferative agents. As shown in Table 2 below, it was confirmed that the 4-(aryl)-N-(2-alkoxythieno[3,2-b]pyrazin-3-yl)-piperazin-1-carboxamide derivative compounds according to Examples 1 to 27 of the present invention were all excellent anti-proliferative agents with an $IC_{50}$ value of less than 2.50 μM, or as low as 0.02 μM.

The invention claimed is:

1. A compound represented by the Formula 1:

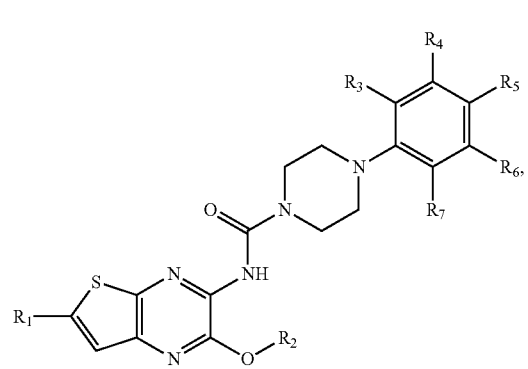

or a pharmaceutically acceptable salt thereof, wherein:
$R_1$ is hydrogen or halogen;
$R_2$ is linear or branched $C_{1-6}$ alkyl; and
$R_3$, $R_4$, $R_5$, $R_6$ and $R_7$ are each independently hydrogen, halogen, linear or branched $C_{1-6}$ alkyl, linear or branched $C_{1-6}$ haloalkyl, $C_{1-6}$ alkoxy, or $C_{1-6}$ haloalkoxy.

2. The compound of claim 1, or the pharmaceutically acceptable salt thereof, wherein $R_1$ is hydrogen or chloro.

3. The compound of claim 1, or the pharmaceutically acceptable salt thereof, wherein $R_2$ is methyl, ethyl, or isopropyl.

4. The compound of claim 1, or the pharmaceutically acceptable salt thereof, wherein $R_3$, $R_4$, $R_5$, $R_6$ and $R_7$ are

TABLE 2

| | $IC_{50}$ (μM) of cancer cell lines | | | | | | | | |
|---|---|---|---|---|---|---|---|---|---|
| Example # | MDA-MB-231 | UMRC2 | PANC-1 | HN31 | A549 | HEK293 | HUVEC | HT29 | SK-OV-3 |
| 1 | 0.02 | 0.03 | 0.53 | 0.27 | 2.13 | 0.63 | 0.12 | 0.31 | 0.27 |
| 2 | 0.06 | 0.08 | 0.95 | 0.99 | <2.50 | 0.93 | 0.91 | 0.62 | 0.82 |
| 3 | 0.04 | 0.06 | 0.56 | 0.71 | 2.11 | 0.87 | 0.54 | 0.53 | 0.85 |
| 4 | 0.63 | 0.54 | 1.28 | 1.54 | <2.50 | <2.50 | 2.25 | <2.50 | <2.50 |
| 5 | 1.22 | 1.72 | 2.32 | 2.35 | <2.50 | <2.50 | <2.50 | <2.50 | <2.50 |
| 6 | 1.13 | 1.21 | 1.98 | 2.10 | <2.50 | <2.50 | <2.50 | <2.50 | <2.50 |
| 7 | <2.50 | <2.50 | <2.50 | <2.50 | <2.50 | <2.50 | <2.50 | <2.50 | <2.50 |
| 8 | <2.50 | <2.50 | <2.50 | <2.50 | <2.50 | <2.50 | <2.50 | <2.50 | <2.50 |
| 9 | <2.50 | <2.50 | <2.50 | <2.50 | <2.50 | <2.50 | <2.50 | <2.50 | <2.50 |
| 10 | 0.02 | 0.03 | 0.38 | 0.18 | 1.14 | 0.56 | 0.06 | 0.27 | 0.23 |
| 11 | 0.07 | 0.07 | 0.24 | 0.41 | 1.31 | 0.65 | 0.07 | 0.31 | 0.27 |
| 12 | 0.05 | 0.04 | 0.24 | 0.33 | 1.28 | 0.55 | 0.07 | 0.30 | 0.29 |
| 13 | 0.16 | 0.26 | 0.65 | 0.72 | <2.50 | <2.50 | <2.50 | <2.50 | <2.50 |
| 14 | 0.34 | 0.57 | <2.50 | 0.65 | <2.50 | <2.50 | <2.50 | <2.50 | <2.50 |
| 15 | 0.25 | 0.25 | 1.12 | 0.78 | <2.50 | <2.50 | <2.50 | <2.50 | <2.50 |
| 16 | 2.12 | <2.50 | <2.50 | <2.50 | <2.50 | <2.50 | <2.50 | <2.50 | <2.50 |
| 17 | <2.50 | <2.50 | <2.50 | <2.50 | <2.50 | <2.50 | <2.50 | <2.50 | <2.50 |
| 18 | <2.50 | <2.50 | <2.50 | <2.50 | <2.50 | <2.50 | <2.50 | <2.50 | <2.50 |
| 19 | <2.50 | 0.25 | 0.58 | 1.12 | 1.52 | 1.23 | 0.68 | 0.71 | <2.50 |
| 20 | 0.25 | <2.50 | 0.36 | 0.36 | 0.15 | 0.12 | 0.21 | 0.62 | 0.22 |
| 21 | 2.21 | 1.74 | 2.12 | <2.50 | 1.63 | 1.25 | <2.50 | 1.85 | 1.85 |
| 22 | 0.52 | 0.21 | 0.63 | 0.45 | 2.21 | 1.12 | 1.36 | 1.12 | 1.36 |
| 23 | 0.36 | <2.50 | 0.58 | 0.28 | 0.63 | 0.35 | 0.45 | 0.28 | 0.36 |
| 24 | 0.12 | 0.36 | 0.44 | <2.50 | 0.87 | 0.25 | <2.50 | 0.36 | 0.12 |
| 25 | 0.15 | <2.50 | 0.08 | 0.17 | 0.22 | 0.36 | 0.13 | 0.25 | 0.63 |
| 26 | <2.50 | <2.50 | <2.50 | <2.50 | <2.50 | <2.50 | <2.50 | <2.50 | <2.50 |
| 27 | <2.50 | <2.50 | <2.50 | <2.50 | <2.50 | <2.50 | <2.50 | <2.50 | <2.50 | each independently hydrogen, fluoro, methyl, trifluoromethyl, methoxy, or trifluoromethoxy.

5. The compound of claim 4, or the pharmaceutically acceptable salt thereof, wherein $R_3$, $R_5$, and $R_7$ are each independently hydrogen.

6. The compound of claim 4, or the pharmaceutically acceptable salt thereof, wherein $R_4$ and $R_6$ are each independently fluoro, methyl, trifluoromethyl, methoxy, or trifluoromethoxy.

7. The compound of claim 1, or the pharmaceutically acceptable salt thereof, wherein the compound is selected from the group consisting of:
1) N-(6-chloro-2-methoxythieno[3,2-b]pyrazin-3-yl)-4-(3,5-dimethoxyphenyl)piperazin-1-carboxamide,
2) N-(6-chloro-2-methoxythieno[3,2-b]pyrazin-3-yl)-4-(3,5-dimethylphenyl)piperazin-1-carboxamide,
3) N-(6-chloro-2-methoxythieno[3,2-b]pyrazin-3-yl)-4-(3,5-difluorophenyl)piperazin-1-carboxamide,
4) N-(6-chloro-2-ethoxythieno[3,2-b]pyrazin-3-yl)-4-(3,5-dimethoxyphenyl)piperazin-1-carboxamide,
5) N-(6-chloro-2-ethoxythieno[3,2-b]pyrazin-3-yl)-4-(3,5-dimethylphenyl)piperazin-1-carboxamide,
6) N-(6-chloro-2-ethoxythieno[3,2-b]pyrazin-3-yl)-4-(3,5-difluorophenyl)piperazin-1-carboxamide,
7) N-(6-chloro-2-isopropoxythieno[3,2-b]pyrazin-3-yl)-4-(3,5-dimethoxyphenyl)piperazin-1-carboxamide,
8) N-(6-chloro-2-isopropoxythieno[3,2-b]pyrazin-3-yl)-4-(3,5-dimethylphenyl)piperazin-1-carboxamide,
9) N-(6-chloro-2-isopropoxythieno[3,2-b]pyrazin-3-yl)-4-(3,5-difluorophenyl)piperazin-1-carboxamide,
10) 4-(3,5-dimethoxyphenyl)-N-(2-methoxythieno[3,2-b]pyrazin-3-yl)piperazin-1-carboxamide,
11) 4-(3,5-dimethylphenyl)-N-(2-methoxythieno[3,2-b]pyrazin-3-yl)piperazin-1-carboxamide,
12) 4-(3,5-difluorophenyl)-N-(2-methoxythieno[3,2-b]pyrazin-3-yl)piperazin-1-carboxamide,
13) 4-(3,5-dimethoxyphenyl)-N-(2-ethoxythieno[3,2-b]pyrazin-3-yl)piperazin-1-carboxamide,
14) 4-(3,5-dimethylphenyl)-N-(2-ethoxythieno[3,2-b]pyrazin-3-yl)piperazin-1-carboxamide,
15) 4-(3,5-difluorophenyl)-N-(2-ethoxythieno[3,2-b]pyrazin-3-yl)piperazin-1-carboxamide,
16) 4-(3,5-dimethoxyphenyl)-N-(2-isopropoxythieno[3,2-b]pyrazin-3-yl)piperazin-1-carboxamide,
17) 4-(3,5-dimethylphenyl)-N-(2-isopropoxythieno[3,2-b]pyrazin-3-yl)piperazin-1-carboxamide,
18) 4-(3,5-difluorophenyl)-N-(2-isopropoxythieno[3,2-b]pyrazin-3-yl)piperazin-1-carboxamide,
19) N-(2-methoxythieno[3,2-b]pyrazin-3-yl)-4-(3-methyl-5-(trifluoromethoxy)phenyl)piperazin-1-carboxamide,
20) N-(2-methoxythieno[3,2-b]pyrazin-3-yl)-4-(3-(trifluoromethoxy)-5-(trifluoromethyl)phenyl)piperazin-1-carboxamide,
21) 4-(3-methoxy-5-methylphenyl)-N-(2-methoxythieno[3,2-b]pyrazin-3-yl)piperazin-1-carboxamide,
22) 4-(3-fluoro-5-methoxyphenyl)-N-(2-methoxythieno[3,2-b]pyrazin-3-yl)piperazin-1-carboxamide,
23) 4-(3-fluoro-5-methylphenyl)-N-(2-methoxythieno[3,2-b]pyrazin-3-yl)piperazin-1-carboxamide,
24) N-(2-methoxythieno[3,2-b]pyrazin-3-yl)-4-(3-(trifluoromethoxy)phenyl)piperazin-1-carboxamide,
25) 4-(3-methoxy-5-(trifluoromethoxy)phenyl)-N-(2-methoxythieno[3,2-b]pyrazin-3-yl)piperazin-1-carboxamide,
26) 4-(3-fluoro-5-(trifluoromethoxy)phenyl)-N-(2-methoxythieno[3,2-b]pyrazin-3-yl)piperazin-1-carboxamide, and
27) 4-(3-fluoro-5-(trifluoromethyl)phenyl)-N-(2-methoxythieno[3,2-b]pyrazin-3-yl)piperazin-1-carboxamide.

8. A pharmaceutical composition comprising as an active ingredient the compound of claim 1, or a pharmaceutically acceptable salt thereof, and a pharmaceutically acceptable carrier or excipient.

9. A method for inhibiting cancer cell proliferation in a subject, comprising administering to the subject the pharmaceutical composition of claim 8.

10. A method for inducing cancer cell apoptosis in a subject, comprising administering to the subject the pharmaceutical composition of claim 8.

11. The method of claim 9 or 10, wherein the subject suffers from a cancer selected from the group consisting of colon cancer, breast cancer, pancreatic cancer, head and neck cancer, kidney cancer, lung cancer and colorectal adenocarcinoma.

12. A process for preparing a compound represented by the Formula 1:

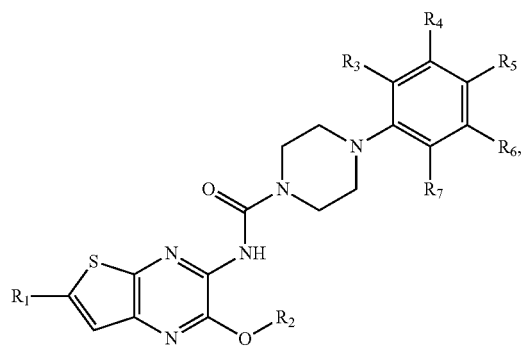

wherein:
$R_1$ is halogen;
$R_2$ is linear or branched $C_{1-6}$ alkyl; and
$R_3$, $R_4$, $R_5$, $R_6$ and $R_7$ are each independently hydrogen, halogen, linear or branched $C_{1-6}$ alkyl, linear or branched $C_{1-6}$ haloalkyl, $C_{1-6}$ alkoxy, or $C_{1-6}$ haloalkoxy;

comprising the following steps:
1) reacting a compound represented by the Formula 2:

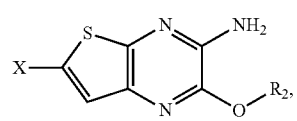

wherein:
X is halogen; and
$R_2$ is linear or branched $C_{1-6}$ alkyl;
with phenyl chloroformate, to obtain a compound represented by the Formula 3:

comprising the following steps:
1) reacting a compound represented by the Formula 2:

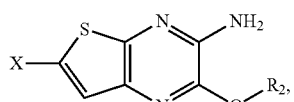

2 wherein:
X is halogen; and
$R_2$ is linear or branched $C_{1-6}$ alkyl;
with ammonium formate in the presence of palladium adsorbed on charcoal, to obtain a compound represented by the following Formula:

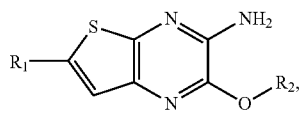

wherein:
$R_1$ is hydrogen; and
$R_2$ is linear or branched $C_{1-6}$ alkyl;
2) reacting the compound represented by the Formula above with phenyl chloroformate, to obtain a compound represented by the Formula 3:

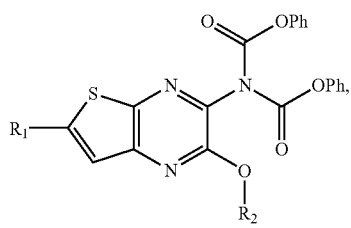

3 wherein:
$R_1$ is hydrogen; and
$R_2$ is linear or branched $C_{1-6}$ alkyl; and
3) reacting the compound represented by the Formula 3 above with a compound represented by the Formula 4:

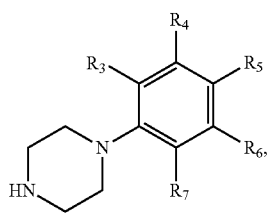

4 wherein:
$R_3$, $R_4$, $R_5$, $R_6$ and $R_7$ are each independently hydrogen, halogen, linear or branched $C_{1-6}$ alkyl, linear or branched $C_{1-6}$ haloalkyl, $C_{1-6}$ alkoxy, or $C_{1-6}$haloalkoxy;
to obtain the compound represented by the Formula 1 above.

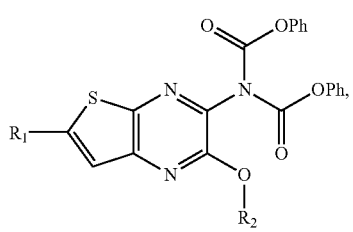

3 wherein:
$R_1$ is halogen; and
$R_2$ is linear or branched $C_{1-6}$ alkyl; and
2) reacting the compound represented by the Formula 3 above with a compound represented by the Formula 4:

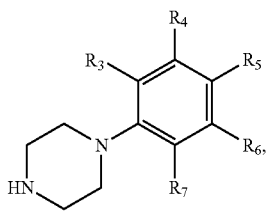

4 wherein:
$R_3$, $R_4$, $R_5$, $R_6$ and $R_7$ are each independently hydrogen, halogen, linear or branched $C_{1-6}$ alkyl, linear or branched $C_{1-6}$ haloalkyl, $C_{1-6}$ alkoxy, or $C_{1-6}$ haloalkoxy;
to obtain the compound represented by the Formula 1 above.

13. The process of claim 12, wherein X is chloro.

14. A process for preparing a compound represented by the Formula 1:

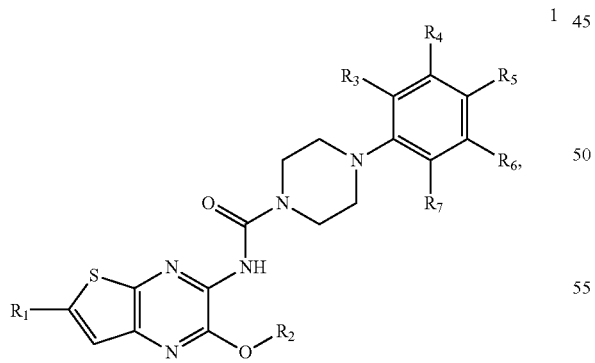

1 wherein:
$R_1$ is hydrogen;
$R_2$ is linear or branched $C_{1-6}$ alkyl; and
$R_3$, $R_4$, $R_5$, $R_6$ and $R_7$ are each independently hydrogen, halogen, linear or branched $C_{1-6}$ alkyl, linear or branched $C_{1-6}$ haloalkyl, $C_{1-6}$ alkoxy, or $C_{1-6}$ haloalkoxy;

15. A process for preparing a compound represented by the Formula 1:

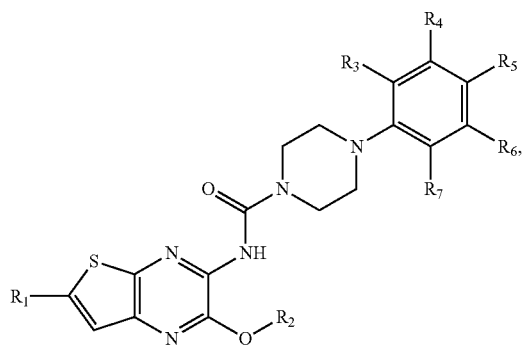

wherein:
 $R_1$ is chloro;
 $R_2$ is methyl; and
 $R_3$, $R_4$, $R_5$, $R_6$ and $R_7$ are each independently hydrogen, halogen, linear or branched $C_{1-6}$ alkyl, linear or branched $C_{1-6}$ haloalkyl, $C_{1-6}$ alkoxy, or $C_{1-6}$ haloalkoxy;

comprising the following steps:
1) reacting a compound represented by the Formula 5:

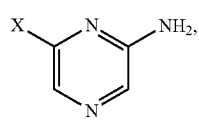

wherein:
 X is halogen;
with N-bromosuccinimide, to obtain a compound represented by the Formula 6:

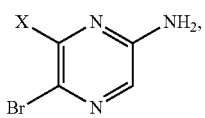

wherein:
 X is halogen;
2) reacting the compound represented by the Formula 6 above with trimethylsilylethynyl, to obtain a compound represented by the Formula 7:

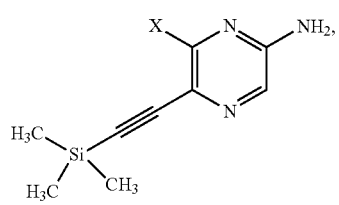

wherein:
 X is halogen;
3) reacting the compound represented by the Formula 7 above with sodium sulfide pentahydrate, to obtain a compound represented by the Formula 8:

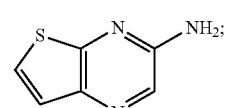

4) reacting the compound represented by the Formula 8 above with N-chlorosuccinimide, to obtain a compound represented by the Formula 9:

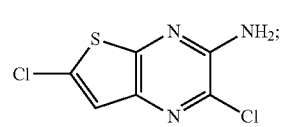

5) reacting the compound represented by the Formula 9 above with sodium methoxide, to obtain a compound represented by the Formula 2:

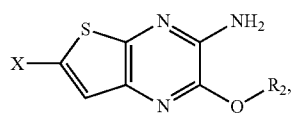

wherein:
 X is chloro; and
 $R_2$ is methyl;

6) reacting the compound represented by the Formula 2 above with phenyl chloroformate, to obtain a compound represented by the Formula 3:

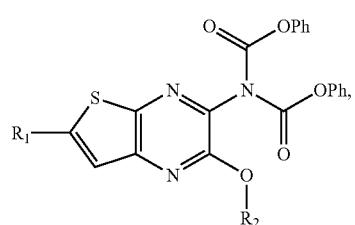

wherein:
 $R_1$ is chloro; and
 $R_2$ is methyl; and 7) reacting the compound represented by the Formula 3 above with a compound represented by the Formula 4:

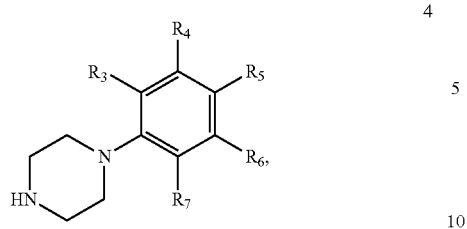
wherein:
R$_3$, R$_4$, R$_5$, R$_6$ and R$_7$ are each independently hydrogen, halogen, linear or branched C$_{1-6}$ alkyl, linear or branched C$_{1-6}$ haloalkyl, C$_{1-6}$ alkoxy, or C$_{1-6}$ haloalkoxy;
to obtain the compound represented by the Formula 1 above.
\* \* \* \* \*